United States Patent
Brown

(10) Patent No.: US 9,157,909 B2
(45) Date of Patent: Oct. 13, 2015

(54) MALE REPRODUCTIVE HEALTH PANEL AND USES THEREOF

(76) Inventor: David B. Brown, Ft. Lauderdale, FL (US)

( * ) Notice: Subject to any disclaimer, the term of this patent is extended or adjusted under 35 U.S.C. 154(b) by 962 days.

(21) Appl. No.: 12/674,201

(22) PCT Filed: Aug. 20, 2008

(86) PCT No.: PCT/US2008/073662
§ 371 (c)(1),
(2), (4) Date: Apr. 12, 2011

(87) PCT Pub. No.: WO2009/026331
PCT Pub. Date: Feb. 26, 2009

(65) Prior Publication Data
US 2011/0262900 A1    Oct. 27, 2011

Related U.S. Application Data

(60) Provisional application No. 60/957,117, filed on Aug. 21, 2007.

(51) Int. Cl.
*C12Q 1/68* (2006.01)
*G01N 33/50* (2006.01)
*A61D 19/02* (2006.01)

(52) U.S. Cl.
CPC ............ *G01N 33/5091* (2013.01); *A61D 19/02* (2013.01); *C12Q 1/68* (2013.01); *G01N 2800/367* (2013.01)

(58) Field of Classification Search
CPC ..................................................... G01N 33/50
See application file for complete search history.

(56) References Cited

U.S. PATENT DOCUMENTS

| | | |
|---|---|---|
| 5,773,217 A | 6/1998 | Wangh |
| 5,919,621 A | 7/1999 | Brown |

FOREIGN PATENT DOCUMENTS

WO   PCT/US2008/73662    8/2008

OTHER PUBLICATIONS

Interna onal Search Report for corresponding PCT/US08/073662 dated Aug. 20, 2008.
Agarwal, et al., Role of Sperm Chromatin Abnormalities and DNA Damage in Male Infertility; Human Reproduction Update, vol. 9, No. 4, pp. 331-345 (2003).
Larson, et al., "Sperm Chromatin Structure Assay Parameters as Predictors of Failed Pregnancy Following Assisted Reproductive Techniques", Human Reproduction, vol. 15, No. 8, pp. 1722-1722, 2000.
Evenson, et al., "Sperm Chromatin Structure Assay: Its Clinical Use for Detecting Sperm DNA Fragmentation in Male Intertility and Comparisons with Other Techniques", Journal of Andrology, vol. 23, No. 1, pp. 25-43, Jan./Feb. 2002.
Virro, et al., "Sperm Chromatin Structure Assay (SCSA®) Parameters are Related to Fertilization, Blastocyst Development, and Ongoing Pregnancy in In Vivo Fertilization and Intracytoplasmic Sperm Injection Cycles", Fertility and Sterilitye, vol. 81, No. 5, pp. 1289-1295, May 2004.
Balhorn, et al., "Aberrant Protamine 1/Protamine 2 Ratios in Sperm of Infertile Human Males", Experientia 44 (1988), Birkhäuser Verlag, CH-4010 Basel Switzerland, Short Communications, pp. 52-55.
Filing Receipt for David B. Brown, "Male Reproductive Health Panel and Uses Thereof", Canadian Patent Application No. 2,697,112, based on corresponding National Phase of PCT/US2008/073662, filed Aug. 20, 2008.
Filing Receipt for David B. Brown, "Male Reproductive Health Panel and Uses Thereof", Mexican Patent Application No. MX/a/2010/002009, based on corresponding National Phase of PCT/US2008/073662, filed Aug. 20, 2008.
Notice of Publication for David B. Brown, "Male Reproductive Health Panel and Uses Thereof", European Patent Application No. 2008798229, based on corresponding National Phase of PCT/US2008/073662, filed Aug. 20, 2008.
Zini et al., "Correlations Between Two Markers of Sperm DNA Integrity, DNA Denaturation and DNA Fragmentation, in Fertile and Infertile Men", Fertility and Sterility, 2001, pp. 674-677, vol. 75, No. 4.
Payne et al., "Redefining the Relationship Between Sperm Deoxyribonucleic Acid Fragmentation as Measured by the Sperm Chromatin Structure Assay and Outcomes of Assisted Reproductive Techniques", Fertility and Sterility, 2005, pp. 356-364, vol. 84, No. 2.
Belloc et al., "Paternal Age and Sperm DNA Decay: Discrepancy Between Chromomycin and Aniline Blue Staining", Reproductive Biomedicine Online, 2009, pp. 264-269, vol. 19, No. 2.
Extended European Search Report dated Sep. 7, 2012 in related European Application No. 08798229.4.

*Primary Examiner* — Valarie Bertoglio
(74) *Attorney, Agent, or Firm* — Denise L. Mayfield; Husch Blackwell LLP

(57) ABSTRACT

A method for assessing male reproductive health is disclosed. In some embodiments, the method comprises screening a sperm sample for sperm DNA accelerated decondensation (SDAD), for sperm DNA fragmentation index (DFI) and/or for delayed sperm DNA decondensation (SDD). The method is useful in the screening and clinical management of reproductively challenged human couples and for assessing reproductive health of potential sperm donors. A method is also provided for selecting an assisted reproductive technology (ART) best suited for a particular donor sperm sample. An automated method for assessing SDAD and SDD test scores is also disclosed, as well as an automated sperm processing protocol for preparing sperm for analysis of SDAD and SDD.

13 Claims, 5 Drawing Sheets

MALE REPRODUCTIVE HEALTH PANEL AND USES THEREOF

RELATED APPLICATIONS

This application is a non-provisional of, claims priority to and the benefit of U.S. Provisional Patent Application Ser. No. 60/957,117, filed on Aug. 21, 2007, the entire contents of which are incorporated herein by reference.

BACKGROUND

Many studies show a decreasing semen quality due to environmental and genetic causes. For example, it has been demonstrated that sperm counts are on the decline, and that other qualitative markers show high sensitivity to these effects, including DNA integrity. Due at least in part to incomplete maturation, cells generate free radicals (reactive oxygen species, ROS). ROS has been reported to cause DNA fragmentation and a loss of sperm function associated with oxidative damage to the sperm plasma membrane and the genetic material, in a sequence that depends on the source of such chemicals. Researchers are now learning that the quality of human sperm is steadily eroding, and might be causing not only infertility in men, but also childhood cancers in the offspring of those who can reproduce (Stewart Irvine, et al, 1996; Irvine D S, 2000; Irvine D S et al, 2000). For the men who can reproduce today, their sub clinically damaged sperm might lead to infertility in their male progeny (Hoyes K P et al, 1994). Continuous exposure to environmental toxins (pesticides, heavy metals, traffic pollutants, organic solvents and vapors, etc.) or electromagnetic radiation may impair sperm quality, affect the genetic integrity of the sperm DNA, or may alter the physiological structure of the sperm severely enough to interfere with the fertilization process (Moline J M et al, 2000; Massaad C et al, 2002). Cigarette smoking is also associated with an increased risk of infertility (Wong W Y et al, 2000; Kunzle R et al 2003). Sperm damage may also be caused by exposure of sperm to heat, such as soaking in hot tubs or hot baths (Karaca A G et al, 2002) or fever. Sperm genetic quality/nuclear integrity has been emphasized for several years as playing a role in early embryogenesis. T thus the rate of success of any assisted reproductive technique (ART) will be benefited where sperm are confirmed to have good DNA integrity.

Since the quality of sperm DNA is an important factor in fertilization and in the selection of spermatozoon for fertilizing an egg (as in intracytoplasmic sperm injection, [ICSI] during in vitro fertilization [IVF]), it is important to sperm quality more objectively, to focus on the assessment on genetic and DNA quality, and to assess late functions of the sperm cell. These factors remain relevant to ICSI procedures. Several methods and techniques have been developed to assess perm function and quality beyond the standard routine tests. The Sperm DNA Decondensation (SDD) Test is one part of a multi-event screening test named the Human Sperm Activation Assay (HSAA). The HSAA is used to examine sperm activation events (DNA decondensation, pronuclear formation, DNA synthesis, and DNA recondensation). The SDD Test is used to assess the process of sperm chromatin/DNA decondensation (Brown D et al, 1992, 1995). Sperm chromatin/DNA decondensation is the first sperm activation event that occurs after a spermatozoon penetrates an ovum (Brown D et al, 1992, Samocha-Bone D. et al, 1998), and is a factor to assess success rate in IVF-ET, ICSI, and other modes of ART. This event is a step in fertilization during which protamine disulphide bonds are reduced to SH, and in which the polycationic protamines combine with the polyanionic egg protein, nucleoplasmin, thus being stripped from DNA, which then combines with histones, allowing the formation of a pronucleus. As the DNA decondenses, the DNA is reformatted such that upon combining with the female's DNA during syngamy, and after the subsequent first cleavage that results in a 2-cell stage embryo, the developmental program is set in motion. A partially reformatted sperm nucleus will have the capacity to initially fertilize the egg, and even under go a number of cell divisions when used in IVF, ICSI, or other ART modes. However, the resulting embryo will not have the capacity to develop to term. Thus, it is important to have pre-ART tests performed to detect males producing sperm with compromised genomic integrity. Without such pre-testing, especially in the cases of IVF and ICSI attempts at pregnancy, the embryologist will often be providing the treating physician with embryos that will not likely develop to term after transfer.

Protamine defects in sperm (genetic or induced) are also correlated with male infertility. It is therefore suggested that the SDD Test provides a probe for the functional integrity of these specific steps in fertilization, and a better predictor of outcome of IVF, especially in the case of ICSI, as well as IUI's or natural inseminations. The test has been applied successfully on both human and rat sperm to detect damage by environmental toxicants, specifically, alkylating agents (Sawyer and Brown, 1995; Sawyer et al, 1998; Sawyer and Brown, 2000). Exposure of the sperm to alkylating agents results in a diminished decondensation. Recently, it has been shown that exposure of the sperm to oxidative stress (reactive oxygen species; ROS) can accelerate the decondensation process (Tirado et al, 2003; Tirado et al, 2004). Hence, both the presence or absence of decondensation must be examined, but likewise, the kinetics/dynamics of the morphological changes are informative.

The process of fertilization involves a series of events including: a) sperm binding to, and then penetration of the oocyte zona pellucida via the acrosome reaction, b) sperm fusion with the oocyte plasma membrane, c) oocyte activation (release of the cortical granules to prevent multiple sperm from fertilizing the egg), d) sperm activation and pronuclear formation (Abou-Haila A. et al. 2000: Furlong, L. et al. 2005).

Sperm activation initiates post-fertilization upon entry into the ooplasm where the compacted sperm DNA undergoes many alterations as it develops into a male pronuclear. During the first phase of sperm activation or decondensation, the chromatin condensation acquired during spermiogenesis is reversed. Protamines are exchanged with histones reformatting the sperm chromatin allowing for pronucleus formation (Ballhorn et al., Wasserman et al.). Once the sperm decondensation is complete, the DNA synthesis phase occurs, that is followed by recondensation of the sperm chromatin in preparation for the cell division that will result in the 2-cell stage embryo (Longo et. al., (1991)).

A need exists in the medical arts for a clinical male screening panel that includes assessment of early sperm activation events, preferably as part of a panel of tests that can be correlated and used in assessing male reproductive health. A need also continues to exist for a more comprehensive male reproductive health panel that may be used to prescribe an assisted reproductive technology (ART) tailored to the particular male patient or animal and/or reproductively challenged couple.

SUMMARY

The present invention, in a general and overall sense, provides an improved male reproductive health panel. Among other uses, the male reproductive health panel finds particular utility and advantage as an improved fertility testing and/or screening method.

In some aspects, the method includes an assessment of the initiation of DNA synthesis in the test sample and an assessment of the rate of sperm DNA chromatin decondensation of the test sample from a test animal, such as a human male. By way of example, an assessment of the initiation of DNA synthesis in the test sample may be made at a 5-minute or 10 minute time point monitoring period. An early onset of the initiation of DNA synthesis in a test sample as observed after a 5 minute or a 10 minute incubation period, as compared to the onset of DNA synthesis of a control sample from a fertile male; DNA synthesis that starts at around the 30 minute incubation time point, provides an indication of impaired or reduced reproductive health in the test animal. Early DNA synthesis is DNA repair synthesis that occurs in sperm recognized as having DNA damage that results in DNA repair pathways being activated. By the way of example, and not intending to be limited to any specific theory or mechanism of action, the observation of this DNA repair synthesis actually may be the result of DNA damage caused by exposure of the male to reproductive toxicants found in the environment and/or workplace, or exposure to some other occupational and/or chemical/radiation related hazard. In addition, DNA damage has been reported as a result of exposure to medications and/or chemicals. Hence, the present methods may indicate a potential exposure and/or side effect to an animal reality from a particular medication or exposure to a particular chemical or group of chemicals in the environment.

Inflammation and/or infection in the testicle(s) results in exposure of the sperm to high levels of reactive oxygen species (ROS). It has previously been reported that exposure of the testicles to high levels of ROS negatively affects male fertility. The present methods may also be used to detect and/or identify infertility resulting from inflammation and/or infection. Medical conditions such as varicocele(s) have also been implicated in reduced fertility, unless surgically removed. Sperm from fertile males not being exposed to any of the above conditions, but that negatively affect DNA integrity, will pass the check points that would activate DNA repair. The normal DNA replication of sperm DNA will typically begin at about the 30 min incubation time point. Thus, identification of the occurrence of early DNA synthesis according to the present methods also provides a sensitive indicator of decreased male reproductive health, and a specific indicator that the male is either being exposed or has been exposed to DNA damaging agents that have compromised sperm DNA integrity.

As a second component of the panel, the percent or amount of sperm DNA fragmentation in a sperm sample may be assessed relative to a measure of sperm DNA fragmentation present in a control sperm sample from a male of normal reproductive health and of proven fertility. For example, the sperm chromatin structure assay; SCSA (Evenson et al. (1980) (Science, 210:11 31-3) and Evenson et al. (1999) Human Reproduction, 14 (1039-49)), also known as the sperm DNA fragmentation assay (SDFA), or the sperm DNA integrity (SDI) Test, may be used to evaluate the amount of broken (fragmented) DNA in a test sperm sample. This assay in some embodiments employs a fluorescent dye, such as acridine orange, which glows red when bound to broken DNA and green when bound to normal (unbroken) DNA. In some embodiments, this step may include analysis of about five thousand (5,000) sperm from the male test animal. The ratio of broken to normal (unbroken) DNA (i.e., red to red+green fluorescence) is determined to provide a DNA fragmentation index (DFI) measure of the male test sample that may be used and compared to the DFI obtained from a known fertile male semen sample. When many fragmented sperm are present with a DFI greater than 30, this is an indication that the male has compromised DNA integrity, and there is an indication of reduced and/or compromised male reproductive health.

In yet other embodiments of the method, a test sample will be examined to monitor when DNA synthesis begins, i.e. the line of DNA synthesis onset. Evidence of early onset of DNA synthesis will provide an indication that DNA repair is occurring, as compared to DNA synthesis that occurs during routine cell replication and fertilization. At 5, 10, 20 and 30 minute incubation time points, samples will be analyzed for the onset of DNA synthesis. The samples that begin DNA synthesis at or around 30 minute time point will be determined to be undergoing normal, non-repair DNA synthesis. The samples that begin DNA synthesis before a 30 minute time point, such as at a 5 minute or a 10 minute time point, will be determined to have early onset of DNA synthesis, and provide a clinical indication that sperm DNA damage has occurred. By way of further explanation, the samples that begin DNA synthesis at or around the 30 minute time point will be determined to have entered into S-Phase of the cell cycle where normal, semi-conservative DNA replication is occurring duplicating the sperm DNA. In a normal fertilized egg, both the male and female pro-nuclei are duplicating their DNA such that after the first division of the zygote, the 2-cell stage embryo will have two daughter cells having identical genomes made up of both the maternal and paternal DNA. Therefore, there is detected evidence of DNA synthesis prior to the 30 minute time point, it can be concluded that this "early" DNA synthesis is not related to the normal sperm DNA replication that occurs after the fertilization of an egg.

These steps provide one embodiment of the presently disclosed male reproductive health panel.

Other embodiments of the panel may include, optionally, an assessment of sperm activation as described in U.S. Pat. Nos. 5,358,847, 5,770,363 and 5,919,621.

Other embodiments of the panel may include yet additional assessment parameters, such as, for example, assessment of exposure of sperm to reactive oxygen species (ROS) activity.

The methods as described herein for assessment of male reproductive health are non-invasive, simple, fast, and provide clinically useful protocol management of a patient as well as for couples seeking to conceive a child by natural or assisted reproductive techniques, including but not limited to one or more of ICSI, IUI, IVF-ET, or any combination of these techniques.

In some embodiments, the step of assessing sperm DNA accelerated decondensation is further described as providing an indication and valuable prediction of the patient sample for resulting in a successful egg fertilization attempt using ICSI (Intracytoptasmic Sperm Injection). For example, with the SDAD step taken at a 5 minute assessment time point, a test score of a semen sample (decondensed sperm DNA amount) that is 120% or more of the value assessed for a sperm control sample (proven fertile male sperm sample)) provides an indication that the test sample would not perform to an acceptable level in an ICSI fertilization attempt of an egg, such as a human or other animal eggs. This step of the method may in some embodiments be described as taking place in a frog egg extract. The egg extract is prepared as described in U.S. Pat. No. 5,358,847, which is incorporated herein in its entirety.

In another aspect of the method, the step of assessing early sperm DNA decondensation may be further described as providing an improved predictive technique for selecting successful assisted reproductive methodology having the greatest or highest probability for success tailored specifically to an individual male's reproductive status. This is distinct from prior assisted reproductive approaches that instead, provide for selection of an assisted reproductive technique based primarily on female reproductive characteristics and/or deficiencies. In this way, selection of the most enhanced opportunity for reproductive success may be based on reproductive health characteristics of both the male and female.

By way of example, the choices between an assisted reproductive approach of ICSI, IUI, or IVF-ET may be made based on the performance of a sperm sample in the described method.

In some embodiments the assay provides for a highly predictive method for identifying males who produce sperm with low fertilizing capacity. Or in the cases where sperm results in a pregnancy, a high probability that the pregnancy will not progress beyond the first trimester, i.e. a low probability of take-home offspring. In one aspect, the present invention identifies such males when their sperm is analyzed in a 5 minute to 10 minute in vitro assay that demonstrates a quantifiable difference between a patient's sperm, and the sperm from a known fertile male. In yet other embodiments, this in vitro assay is the sperm DNA accelerated decondensation (SDAD) Test. In other embodiments, the in vitro assay is the sperm early DNA synthesis (SEDS) Test. In yet other embodiments, the methods include the SDAD Test, SDD Test, and SEDS Test.

In another aspect, a sperm screening method is provided that is more highly predictive of a take-home baby likelihood when using an identified assisted reproductive technique (ART). By way of example, such as assisted reproductive technique may be by the intracytoplasmic sperm injection (ICSI) technique. The presently disclosed methods provide a predictive value of a tested male's relative measure of reproductive health, that is highly statistically significant ($p<0.01$).

In some embodiments, a screening method is provided that is useful in identifying male sperm donors who will have a low probability of successful ART attempts at pregnancy (success being defined as live birth), such as when using ICSI. Other sperm screening assays, such as the sperm DNA decondensation (SDD) Test, the sperm penetration assay (SPA) and the sperm chromatin structure assay (SCSA) have all been found not to be predictive of ICSI live birth outcome. Thus, in some aspects, the present disclosure describes a screening method that can predict ICSI outcome. In other embodiments, this screening method comprises obtaining a semen sample from a potential sperm donor that has been determined as providing a normal sperm assay result in a SPA and SDD Test, and assessing the sample for sperm DNA accelerated decondensation (SDAD) in a frog egg extract as described herein. In some embodiments, the sperm DNA accelerated decondensation (SDAD) is a measure of chromatin DNA decondensation evidenced after about a 5 (five) minute incubation interval in a frog egg extract. In other embodiments, a sperm sample with essentially complete sperm chromatin DNA decondensation at the five (5) minute time interval identifies an unsatisfactory sperm donor for an ICSI pregnancy attempt.

In some embodiments, a screening method is provided for identifying a male sperm donor having a low probability of a successful ART attempt at pregnancy (such as by an IUI and IVF assisted reproductive technique). In some embodiments, the screening method comprises obtaining a semen sample from a potential sperm donor that has been determined to have an abnormal SDD Test score (a delay in DNA decondensation when incubated in frog egg extract). In other embodiments, the delay in sperm DNA decondensation is a measure of chromatin DNA decondensation evidenced after about a 15 (fifteen) minute incubation interval in a frog egg extract. In other embodiments, a sperm sample with an abnormal response in the SDD Test identifies an unsatisfactory sperm donor for an IUI and/or IVF pregnancy attempt. Because the SDD Test has been identified in the present panels as having no predictive capacity for determining if a patient will succeed in an ICSI attempt at pregnancy, such patients who do not have any expected success for producing a fertilization event by IUI or IVF can be immediately counseled and/or directed to the use of an ICSI assisted reproduction option.

In yet another aspect, the invention provides an automated sperm screening assay for assessing male reproductive health. In some embodiments, the automated sperm screening assay may be described as providing for the scoring of large numbers of sperm animal samples simultaneously. In some embodiments, the automated assay is a high throughput sperm screening method that employs a 96-microtiter well plate, each plate comprising a volume of a frog egg extract. Optionally, and in some embodiments, each microtiter well plate may include frog egg extract containing a DNA labeling agent, such as tritiated thymidine triphosphate (when autoradiography is used to analyze DNA synthesis) or 5-Bromo-2'-deoxyuridine (BUdR), when sperm will be stained with a fluorescent tagged anti-BUdR antibody, and the DNA synthesis analyzed using an automated system/image analysis system described herein. Once the extract sperm mixture is incubating, aliquots will be removed at 5 minutes (SDAD Test), and 15 minutes (SDD Test) and the sperm in these aliquots fixed and stained for subsequent analysis as described herein, and scored using an image analysis system. In another embodiment sperm, in an additional aliquot will be analyzed manually using phase contrast microscopy at a 5 minute time point (SDAD Test) and a 15 minute time point (SDD Test), as described herein.

In other embodiments, the male reproductive health panel comprises a sperm screening assay comprising an SDAD sample assessment and an SDD sample assessment.

In another embodiment, a method is described for using the SDD Test to identify an unsatisfactory sperm donor whose abnormal score is determined to be related to the patient also having a varicocele(s). When identified, such individuals have been found to benefit from a varicocelectomy. A reversed and/or improvement in the patient's reproductive health and reproductive potential may be conducted by use of the herein described SDD test. If a normal SDD test result from the post varicocelectomy patient is obtained, then the patient will be identified as suitable for an assisted reproductive procedure.

The following definitions are used throughout the description of the present invention:

As used in the description of the present invention, the term, "hyperdecondensed sperm" is defined as sperm with a 2-fold increase in size over that observed in the fully decondensed sperm. As used in the present description, a "successful" pregnancy is defined as a live birth resulting from a pregnancy achieved using an assisted reproductive technique (ART).

As used in the description of the present invention, the term, "reproductively challenged couple" is defined as a human male and a human female that have been involuntarily infertile for 1 or more years. Approximately forty percent (40%) of these couples are infertile due to male factor(s), forty percent (40%) are infertile due to female factor(s), and 20% are infertile due to combined male and female factors.

Reproductive health is defined for purposes of the present invention as including, but not limited to, fitness of the male as a sperm donor based on the relative fertilizing capacity of sperm obtained from the male.

As used in the description of the present inventor, the term, "take-home baby" is defined as a live human birth.

The following abbreviations are used throughout the description of the present invention.

The following abbreviations are used throughout the description of the invention:

LPO=lipid peroxidation
SEDS=sperm early DNA synthesis;
HSAA=human sperm activation assay;
SDAD=sperm DNA accelerated decondensation assay;
ROS=reactive oxygen species;
PBS=phosphate buffered saline
ICSI=intracytoplasmic sperm injection
SDD=sperm DNA decondensation
MDA=Malondialdehyde
4-HNE=4-hydroxynonenal
NBT=nitroblue tetrazolium
PMNL=polymorphonuclear leukocytes
ART=assisted reproductive technology
PMA=phorbol-12 myristate-13 acetate
HOST=hypo-osmotic swelling test
WHO=World Health Organization
HHE=4-hydroxy-2hexenal
SDD=sperm DNA decondensation
ROS=reactive oxygen species
SPA=sperm penetration assay
SCI=sperm capacitation index
ODR=outcome delivery rate
OR=odds ratio
PPV=positive predictive value
4-HA=hydroxyalkenals
VX=variocelectomy
SC=spontaneous conceptions
SCSA=sperm chromatin structure assay
SDFA=sperm DNA fragmentation assay
IUI=intrauterine insemination
IVF=in vitro fertilization
$H_2O_2$=hydrogen peroxide
BUdR=5-Bromo-2'-deoxyuridine
$H^3$-TTP=tritiated thymidine triphosphate

(A-E) Normal responses (control untreated sperm). (a-e) Sperm exposed to 100 μM $H_2O_2$ for 1 hr. (A and a) Sperm at time zero before incubation in the egg extract. (B and b) Sperm after a 5 min incubation in egg extract. Notice that sperm exposed to 100 μM $H_2O_2$ for 1 hr had an early initiation of DNA synthesis (b). (C and c) Sperm after a 15 min incubation in the egg extract. Again, notice the early initiation of DNA synthesis in sperm exposed to 100 μM $H_2O_2$ for 1 hr (c). (D, d and E, e) Sperm after a 2 and 3 hr incubation in egg extract, respectively. (D and E) Untreated control sperm nuclei undergo recondensation with regular consistency in size, shape, and no early initiation of DNA synthesis. However, sperm exposed to 100 μM $H_2O_2$ for 1 hr can be seen to show irregular recondensation, aggregation, differences in size and shape, as well as the presence of sperm arrested in a hyperdecondensed state (d and e).

Figure 4A:
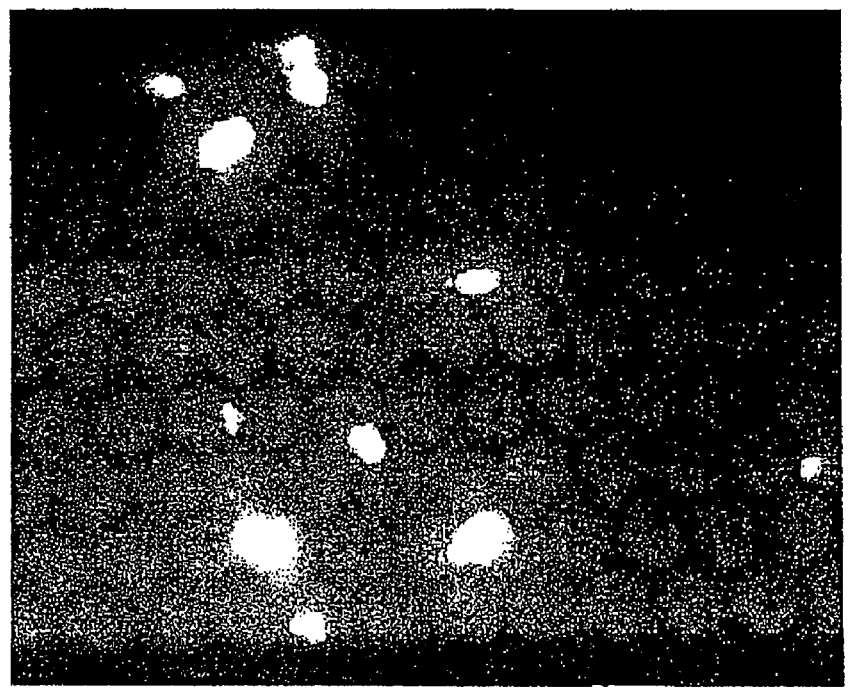
Figure 4B:
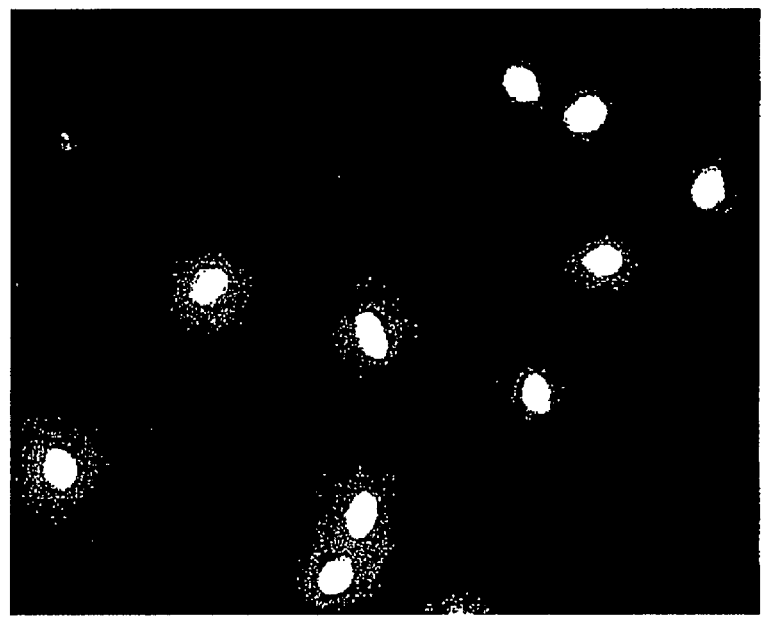

FIG. 4: Data fields of images captured and analyzed using an image analysis system; FIG. 4a—Abnormal SDD response: Phase contrast SDD Test Score=44.8: Image Analysis scoring of 356 cells=38.9; Note the microwells etched into the glass that the sperm settles on or in providing for a large number of single sperm (not clumped together as 2 or more cells) that can be quickly and accurately analyzed. When you change fields you must refocus before capturing the images. Hence, the automatic focusing system described in FIG. 4b—Normal SDD Response: Phase contrast SDD Test Score=94.4: Image analysis scoring of 218 cells=93.9.

Figure 5:
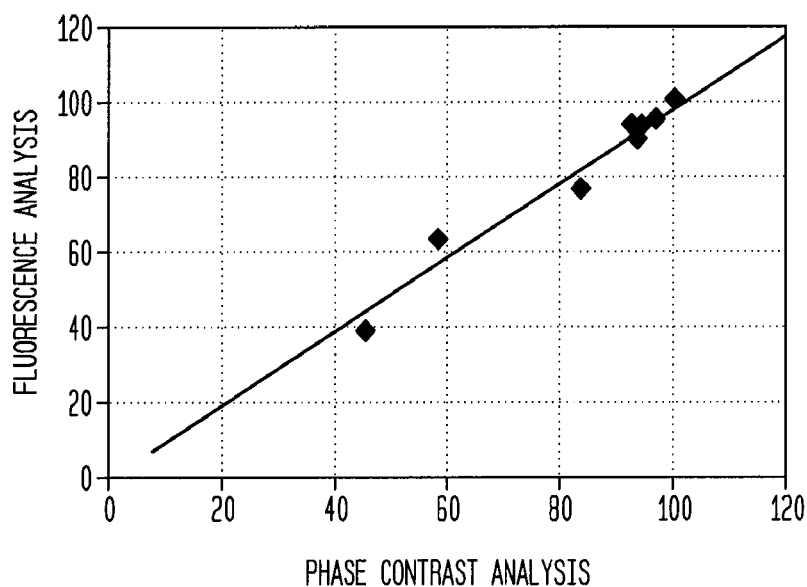

FIG. 5: Comparison of SDD Test results obtained when scoring in real time manually using phase contrast microscopy, with results obtained when scoring using an image analysis system (fluorescence microscopy). The 2 scoring approaches provide essentially identical results (correlation coefficient=0.9831)

DETAILED DESCRIPTION

The invention relates to a male reproductive health panel and uses thereof.

In some embodiments, the method includes a step of monitoring sperm from the male partner of a male/female couple experiencing infertility challenges for an accelerated rate of sperm DNA decondensation as compared to a control sperm sample from a fertile male known to have normal sperm DNA decondensation as determined with the methods disclosed herein. For example, a test sperm sample will be monitored to determine if the sample sperm demonstrates an accelerated rate of DNA decondensation achieving a defined percentage of sperm DNA decondensation greater than observed when compared to a normal control sperm sample. This method step is described herein as the sperm DNA accelerated decondensation (SDAD) Test.

In other embodiments, the method includes a step of monitoring sperm for a delayed rate of sperm DNA decondensation of a test sperm sample, as compared to a normal control sperm sample. For example, a test sperm sample will be monitored to determine if the sample sperm evidences a delayed rate for achieving a defined percentage of sperm DNA decondensation (SDD) as compared to a control sperm sample. This method is described herein as the sperm DNA decondensation (SDD) Test.

In other aspects, methods are provided for identifying an appropriate assisted reproductive technology (ART) for a selected sperm specimen. The method provides for individualizing the treatment for reproductively challenged couples to include male-specific criteria associated with male fertility or the lack thereof. In particular embodiments, a shortened (e.g. 5 minute) time point is employed in the assay for accelerated sperm DNA decondensation assessment (SDAD Test), and a 15 minute time point is employed in the assay for delayed DNA decondensation assessment (SDD Test) as part of the method.

The invention also provides a high-throughput method for clinical sperm assessment, wherein the SDAD and SDD Tests are performed as part of an automated system employing fluorescence microscopy. The SDD Test is predictive for failure in IUI and IVF attempts at pregnancy, but is not predictive of failure for ICSI attempt of pregnancy. The SDAD Test is predictive of sperm samples that have low probability for success in ICSI ART attempts at pregnancy, and is the only test available that can identify such patients. These sperm samples are demonstrated herein to be normal in the SDD Test. Thus, an abnormal reading in the SDD Test (an abnormal score) may be used to identify sperm samples and patients having a higher probability of reproductive success using the assisted reproductive approach of ICSI. Such patients would be directed immediately to ICSI as their chances of success in IUI and IUF attempts at pregnancy are significantly lower.

The invention also provides a method to identify males who can benefit from a varicocelectomy. Such individuals, upon finding their SDD Test results are abnormal, and having a Urologist find a varicocele(s) will benefit from a varicocelectomy. After the varicocelectomy is performed, the patient will be given 3-6 months to heal. When a significant improvement in a subsequent SDD test post-surgery is found, such individuals will have an improved chance for fathering children by natural conception or ART.

Various modifications and changes can be made to the teachings herein without departing from the spirit and scope of the invention.

The following examples are provided to demonstrate various aspects and methods of the invention, and are provided to enhance the understanding of the methods described herein. The following examples are in no manner intended to limit the scope of the inventive methods and/or their clinical or other applications.

Example 1

Sperm DNA Accelerated Decondensation (SDAD) Test Scores Can Predict ICSI Live Birth Outcome. However, Both the Sperm DNA Decondensation (SDD) Test and Sperm Penetration Assay (SPA) Scores do NOT Predict ICSI Live Birth Outcome Sperm DNA integrity testing has been reported to predict failure of sperm with assisted reproductive technology (ART), regardless of the method of insemination. However, as the methods for isolating the 'prime' sperm from the total population of sperm in a semen sample have improved, and the embryos resulting from IVF and ICSI are now monitored for 5 days before transferring into the female, recent clinical studies have shown that the sperm DNA structure tests of DNA integrity (SCSA/SDFA/DFI) can identify reduced chances for success in some ART methods, such as intrauterine insemination (IUI), but are no longer predictive of IVF or ICSI success. The objective of this present study was to determine if the sperm penetration assay (SPA) and the sperm DNA decondensation (SDD) Test; both previously reported to predict live birth outcome in all forms of ART, still have this capacity.

Previous work indicated that accelerated DNA decondensation is observed in sperm exposed to higher than normal levels of reactive oxygen species (ROS) both in vitro and in vivo (Ref). When performing this study, accelerated DNA decondensation was evaluated to determine if this test (sperm DNA accelerated decondensation (SDAD) Test) is predictive of a successful ICSI outcome. The SDAD Test measures the fraction of cells fully decondensed after a 5 minute incubation in frog egg extract, measuring accelerated decondensation. This study was to review the pregnancy outcome in ICSI cycles in relation to the SDAD Test results and determine if the SDAD Test has predictive capacity for determining failure in ART.

Materials and Methods

A prospective, double blinded, single center, cohort study (n=60 couples)

Outcome was evaluated by delivery rate (ODR), defined as the number of ongoing pregnancies and/or deliveries per ICSI cycle.

The males were from couples where the male partners were admitted for andrology evaluation including the SPA in preparation for IVF. Measurements were performed using sperm from the same ejaculate used for each couple's ICSI attempt at pregnancy.

Statistics for success rates when performing ICSI:
70% Fertilization Rate
45-50% Pregnancy Rate
40% Live Birth Rate Patients Male Age 25-45. Female age: 25-40. Male partners of infertile couples who fulfill the inclusion and exclusion criteria were included in the study.

Study groups whose samples were analyzed in both the SDD Test and SPA (Example 3), and in the SDAD Test (this example), as well as ICSI attempts at pregnancy.

Study Group

Infertile males from infertile couples for whom SPA would have been prescribed, either leading to IVF treatment or as part of IVF pre-evaluation. This group was divided into 3 subgroups based on previous SPA results obtained using non-gradient prepared sperm when performing the SPA:
Highest SCI>6,
Highest SCI 1.0-6,
Highest SCI<1.0.

Inclusion Criteria

Female partner was checked for the following:

Infection with microorganisms (viral, bacterial or fungal such as *Mycoplasma/Ureaplasma, Chlamydia trachomatis*, Bacterial Vaginosis) known to be associated with female infertility (Past or Current).

Autoimmune disease (lupus, RA, MS, Diabetes, Hashimoto, etc.) determined while interviewing the infertile couple.

Inflammatory/autoimmune/coagulation blood feature abnormalities as assessed by blood work including tests for Lupus anti coagulant (LAC), Anti cardiolipin Antibodies (ACA), Anti phospholipid antibodies (APA), Natural Killer Cells (NK), Reproductive immunophenotyping (RIP), Anti Microsomal Antibodies (thyroid marker) (AMA) and Factor V (coagulation).

Blood for workup for the female was sent up to 6 weeks prior to beginning the cycle. One plasma sample (sent frozen) was used in the assay of Factor V and LAC. One heparinized whole blood sample (sent at ambient temp) was used for cellular immunology testing. One serum sample (sent at ambient temperature) was used in the ACA, APA and AMA tests.

Oligo or normospermic male with >5 million total motile sperm.

Exclusion Criteria
  Age: Patients/donors younger than 25 y or older than 45 years.
Control Group
  Healthy fertile semen donors used as controls in the SPA and in the SDD and SDAD Tests.
Patient Recruitment
  The prospective study enrolled couples who fulfilled the selection criteria.
Main Outcome Measures
  Diagnostic:
  For each patient, the following was be measured:
  Standard andrology work-up including concentration of sperm, morphology of sperm, volume of ejaculate, and motility of the sperm in all specimens used for the study.
  Sperm DNA accelerated decondensation in the SDAD Test (5 min).
  Sperm DNA delayed decondensation in the SDD Test (15 min).
  Fertilization rates, clinical pregnancy rates, successful pregnancies as defined by any pregnancy continuing past 13 weeks, live births, and the child assessment results at birth.
  Pregnancy complications, and gestation week if ended.
Details of the Protocol
  Semen Samples:
  60 patients participated in this study. Specimens were allowed to liquefy by incubating up to 1 hr at room temperature (not less than 22° C.). Specimens were evaluated on-site in the andrology lab for basic parameters
The Protocol
  The sperm from the 60 patients was split into 3 aliquots:
  Aliquot A) A semen sample from each patient containing at least 2 million sperm were kept in the refrigerator at 2-8° C., until shipped cold by packing with a coolpak. Specimens were sent no later than 9 days after sample collection. The samples were analyzed in the SDAD and SDD Tests within 14 days of sample collection. Any sample arriving such that it could not be analyzed within the 14 day QC window was rejected, and another sample requested.
  Aliquot B) semen containing ~2 million sperm was passed through a density gradient and prepared following the protocol for preparing sperm for an ICSI attempt at pregnancy.
  Aliquot C) The remainder of the semen sample was cryopreserved for future use in ICSI attempts at pregnancy.
  The above protocol was followed that allowed us to determine the scores for the SDD and SDAD Tests, and the SPA using the same sperm that was subsequently used in an ICSI attempt at pregnancy.
  All samples for analysis were blinded.
  Only the patient's initials and date of birth information was provided for tracing and recording purposes. None of the other andrology test results were provided at the time of test submission. The study was unblinded for each patient 13 weeks after each patient's sample was used in an ICSI attempt at pregnancy. The patient's pregnancy outcomes and were disclosed as soon as the results were available; results used in the comprehensive statistical analysis that was done after all samples were unblinded.
Preparation of Sperm for Analysis in the SPA
  Semen was washed and concentrated by the gradient method. After gradient preparation the sperm was resuspended in sperm wash medium and diluted 1:1 with Test Yolk Buffer (TYB). The sperm/TYB mixture will then be slowly cooled to 2-8° C. and stored at this temperature for 2-3 days. After this time, sperm wash medium at 37° C. was added to the cold sperm/TYB mixture, providing a thermal shock. After the sperm/TYB had incubated for 30 min at 37° C., the mixture was centrifuged for 10 min at 600 g. The supernatant was then removed, up to 1.0 mL sperm wash medium added, and the sperm allowed to incubate for 60 min at 37° C. The sperm were adjusted to a concentration of 5 million total motile sperm/mL. Egg Extracts:
  Female *Xenopus Laevis* Oocyte positive frogs were used to obtain unfertilized eggs used to make the frog egg extract used in performing the SDAD and SDD tests. The process used to obtain the eggs does not harm the frogs, and the frogs can be used to obtain eggs every 6-8 weeks. After preparing the frog egg extract, the extracts were immediately snap deep-frozen in liquid $N_2$ (LN) and placed in cryovials in LN until used for performing the tests. This frog egg extract was used to induce sperm DNA decondensation in vitro, mimicking the post-fertilization sperm activation events that would have occurred had the sperm fertilized an egg in vivo.
The SDD and SDAD Tests
  Controls: In each test one negative control and one positive control will be run in parallel with the patient samples. The control specimen is a normal, SDD pre-tested specimen from a sperm bank, or a specimen obtained from an individual who has produced 4 or more ejaculates containing sperm that respond normally at the 15 min time point. This control serves as negative control when used in the complete SDD Test protocol. Patient positive controls that have been identified as being abnormal in routine testing of patient samples sent for analysis in the SDD Test are frozen and used as the positive control.
  The SDD Test was performed as described by Brown et al. (1992, 1995) with the new addition of the 5 minute time point to score for accelerated DNA decondensation. (The SDAD Test).
The Test
  About two million sperm per sample were washed and permeabilized. After four extensive washes with special buffers, the sperm were treated with a dithiotreitol (DTT)-containing buffer. The DTT-treated sperm were incubated with frog egg extract to induce sperm DNA decondensation. After a 5 min incubation (SDAD Test), an aliquot was taken from the sperm-egg incubation mixture, and placed on a glass slide with a cover slip. Phase contrast microscopy was used to score 50-100 sperm from a fertile male (the number of sperm that can be scored in a 5 min window in real time), After a 15 min incubation (SDD Test), an aliquot was again taken from the sperm-egg incubation mixture, and placed on a glass slide with a cover slip. Again, using Phase contrast microscopy 50-100 sperm from a fertile male were scored during a 5 minute window in real time. the above protocol was repeated for each patient sample. The percentage of sperm undergoing full decondensation was recorded. The raw data was normalized with the negative control decondensation value yielding the reportable value as % of the control.
Outcome Evaluation
  All the results were statistically evaluated including but not limited to:
  Correlation between the SPA scores and pregnancy outcomes of the 60 ICSI attempts at pregnancy.
  Correlation between the SDAD Test scores and pregnancy outcomes of the 60 ICSI attempts at pregnancy.
  Correlation between the SDD Test scores and pregnancy outcomes of the 60 ICSI attempts at pregnancy.
  Correlation between SPA scores and pregnancy completion: A significant correlation was not observed. We evaluated the odds ratio (OR) and positive predictive value (PPV) for ICSI failure to further verify the results.
  Correlation between SDD Test scores and pregnancy completion: A significant correlation was not observed. We evaluated the odds ratio (OR) and positive predictive value (PPV) for ICSI failure to further verify the results.

Correlation between SDAD Test scores and pregnancy completion: Evaluation of the cut off value (% of the control) for the SDAD Test that best predicts pregnancy failure, including an evaluation of the odds ratio (OR) and positive predictive value (PPV) for ICSI failure.

Determination of the best cutoff value predicting pregnancy failure or specific pregnancy outcomes was done by ROC analysis. Specificity, Sensitivity, PPV and NPV as well as Accuracy were evaluated using the selected cutoff values.

Statistical Analysis

Statistical Significance was assessed by $Chi^2$ distribution with a P value of <0.05 being considered statistically significant.

Normal SDAD test scores were determined to be scores less than 120% of a control sperm sample. Accelerated sperm test scores were determine to be scores of 120% or greater than a control sperm sample from a proven fertile male. (i.e., fertile denotes a sperm sample/donor having a history of a successful pregnancy producing event).

SDAD Test Results

TABLE 1

Treatment outcome as a function of SDAD in a group of ICSI cycles (n = 60)

| | SDAD (% of Control) | |
|---|---|---|
| | <120 | ≥120 |
| ICSI cycles | 47 | 13 |
| Delivered Pregnancies | 24 | 0 |
| Outcome Delivery Rate (ODR) | 51.1%%[1] | 0%[1] |
| Embryos transferred (average) | 1.9[2] | 1.8[2] |
| P | <0.001 | |
| Odds Ratio (OR) of failing ICSI when SDD Test score is positive | 0 | |
| Positive Predictive Value (PPV) | 100% | |

[1]Statistical Significance was assessed by $Chi^2$ distribution
[2]Not Significant SPA Results Outcomes of cycles with a SPA SCI<14 (n=23) were compared to cycles with a SPA SCI≥14 (n=37). The ODR was (10/23) 43.4% vs (15/37) 40.5% (p>0.05), respectively.

SDD Test Results: Outcomes of cycles with a SDD<80 (n=26) were compared to cycles with a SDD>80 (n=34). The ODR was (10/25) 40.0% vs (15/35) 42.9%, respectively.

TABLE 2

Treatment outcome as a function of SDD Test and SPA in a group of 60 ICSI Cycles.

| | SDD (%) | | SPA (gradient SCI) | |
|---|---|---|---|---|
| | <80 | ≥80 | <14 | ≥14 |
| ICSI cycles | 25 | 35 | 23 | 37 |
| Ongoing/delivered pregnancies | 10 | 15 | 10 | 15 |
| Delivery rate (ODR) | 40.0% | 42.9% | 43.4% | 40.5% |
| OR | | 1.07 | | 93.9 |
| P | | >>0.05 NS | | >>0.05 NS |
| PPV | | 60% | | 56.6% |

Conclusions

The SDAD Test, 5 minute accelerated DNA decondensation IS predictive of outcome delivery rate (ODR) in IVF cycles with ICSI.

The SPA with gradient preparation is NOT predictive of ODR in IVF cycles with ICSI.

The SDD Test, 15 minute delayed DNA decondensation is NOT predictive of ODR in IVF cycles with ICSI.

Example 2

Sperm DNA Decondensation (SDD) Test and Selection of Assisted Reproductive Technology Method Sperm DNA integrity testing has been reported to predict failure of sperm with assisted reproductive technology (ART), regardless of the method of insemination. However, as the methods for isolating the 'prime' sperm from the total population of sperm in a semen sample have improved, and the embryos resulting from IVF and ICSI are now monitored for 5 days before transferring into the female, recent clinical studies have shown that the sperm DNA structure tests of DNA integrity (SCSA/SDFA/DFI) can identify reduced chances for success in some ART methods, such as intrauterine insemination (IUI), these tests are no longer predictive of IVF or ICSI success. Similarly, the sperm DNA decondensation (SDD) Test; a sperm function test, has previously been shown to predict failure in subsequent ART attempts, regardless of method. The goal of this example is to demonstrate that the SDD Test has a predictive capability in current IUI and IVF insemination protocols, but as was found for the sperm structure tests, is no longer predictive of ICSI outcome. Methods: A retrospective review was performed on every male with SDD testing within a single fertility practice.

Outcomes were identified for the first IUI or IVF attempt subsequent to SDD testing. A successful ART attempt was defined as presence of fetal heart beat at 8-10 weeks gestation or live delivery. Outcome of IUI or IVF was correlated with SDD score. An abnormal SDD score was defined as less than 80% of the control and normal was defined as 80% of the control or higher. There were no exclusions for female other male factor etiology.

Results

SDD scores and first IUI or IVF attempt outcome data was available for 58 males. Forty-three males had normal SDD scores and had a 22% success rate with IUI (N=23) and 35% with IVF (N=20) attempts. Fifteen males had abnormal SDD scores with 0% successful outcome with IUI (N=6) and IVF (N=9) attempts. The difference between the 28% success rate of SDD normal patients (N=43, IUI/IVF combined) and 0% with SDD abnormal patients (N=15, IUI/IVF combined)) was statistically significant using Fischer's exact test (P=0.0325) (Odds Ratio>5). An additional 18 patients underwent IVF with ICSI where 81% (N=16) of males with normal SDD scores had success and 100% (n=2) with an abnormal SDD had success, although there was not sufficient statistical power to conclude that the groups were different. There was no significant difference for the average age and FSH levels of female partners between SDD normal and SDD abnormal groups.

In several prospective blinded studies performed in the 1990s (Brown D B., et al. Yale J. of Biology and Medicine 1992 (65):29-38; Brown D B., et al. Fertility and Sterility 1995 (64):612-622) with n=74 inexplicably infertile men demonstrated that 20% had abnormal SDD scores and no success with IUI, IVF, or GIFT, while only 1.4% of fertile men (n=74) had abnormal SDD Test scores. In two recent prospective studies described in Examples 1 and 3 demonstrated that males with abnormal SDD Test scores had success rates comparable to males with normal SDD Test scores when using current ICSI methodologies.

Conclusion

Based upon the present data analysis, the SDD Test will identify male patients with reduced chances of success with IUI and IVF who may benefit from earlier consideration of ICSI.

Example 3

SDD Test and the SDFA Scores Predict ICSI Outcome and Use of these Tests in an Advanced Sperm Panel to Maximize Consideration of ICSI Early in Patient Treatment The present example demonstrates the utility of the combined use of the SDD Test and the SDFA for fertility specialists. Specifically the present method and example of same provides the reproductive health counselor/manager with information in optimizing a treatment strategy. This information is no provided by the use of either test alone (SDD or SDFA).

The Study

Perform the SDD Test and SDFA on a patients sample and see if the scores predict ICSI outcome.

SDD Test: Performed as described in Example 1.

The Sperm DNA Fragmentation Assay (SDFA); the other test that will be used in this study, determines if the DNA fragmentation of a patient's sperm sample is above what is normally seen in normal fertile males. If the sperm with DNA fragmentation are significantly higher in number than what is found for the sperm in a normal sample, then this sample has a lower potential for achieving pregnancy and eventually producing a live birth; the higher the percentage of sperm with fragmentation, the lower the potential for achieving pregnancy (Larson, K L et al., 2000; Evenson, D P et al., 2002; Virro, M R et al., 2004). The SDFA uses the same methodology as the Evenson Sperm Chromatin Structure Assay (SCSA). The SDFA utilizes Acridine Orange (AO) as a fluorescent DNA probe and employs flow cytometry to measure the intensity of fluorescence. AO is a cell-permeant nucleic acid binding dye that emits green fluorescence when bound to normal DNA and red fluorescence when bound to damaged DNA. After low pH treatment in situ, primarily to dissociate the protamines, sperm DNA that is damaged displays more single stranded DNA and will fluoresce red, while sperm DNA that is not damaged displays more double stranded DNA and will fluoresce green. For each sample, 5000 cells are measured and the ratio of red to total fluorescence is calculated. The percentage of sperm with high DNA fragmentation (the calculated ratio) is expressed as the DNA Fragmentation Index (DFI; Evenson, D P et al., 2002). The prevalence of cells staining intensely for dsDNA (HDS) reflects elevated proportions of immature sperm and is also part of the quantitative report.

Although both the SCSA/SDFA and the SDD Test; advanced bioassays for sperm function and quality have been established for many years, they have not yet been widely applied in clinics as an advanced sperm panel for diagnosing the male factor infertility due to the following reasons:

1) Insufficient definition of the precise clinical indications.
2) Incomplete comparison as to differences, complementarities or superiority of these specific tests relative to each other.

Study to Demonstrate SDD Test Scores are not Predictive of ICSI Outcome (P=0.6629)

Design: Double blinded study:

Couples: 66 couples total enrolled in study. Of these:

58 couples with SDD scores and ICSI outcome; 51 couples with SDFA test scores and ICSI outcome; 42 couples with SDD test and SDFA scores and ICSI outcome.

Study to Demonstrate SDFA Test Scores are not Predictive of ICSI Outcome (P=0.7665)

DNA fragmentation index (DFI)

n=30 (Normal scores less than 30); Outcome: 10 pregnancies past $1^{st}$ trimester=31.8% n=21) Abnormal scores greater than 15), Outcome: 2 pregnancies past 1st trimester=28.6%

Study to Demonstrate High Density Staining (HDS) Analysis. No Utility in Predicting ICSI Outcome, p=0.9749 n=44 (Normal scores less than or equal to 15. Outcome: 14 pregnancies past $1^{st}$ trimester=31.8% n=7 (Abnormal scores greater than 15). Outcome: 2 pregnancies past $1^{st}$ trimester=28.6%.

Conclusion

In order to direct patients who might benefit from earlier consideration of ICSI attempts at pregnancy, both the SDD Test and SDFA should be performed pre-ART.

Example 4

Automation of Scoring the SDAD and SDD Tests

The present example employs Optical LiveCell Array technology.

The present example demonstrates one embodiments of the method that includes a 96 well plate with etched glass at the bottom of each well with a transparent array of micron-sized wells, with sperm analysis as one application is provided. This plate will be used in the practice of the present example to accommodate the running of 8 assays at the same time and then transfer stained, fixed sperm into 8 wells at a time speeding up the processing of the samples. The image analysis system can then be used to analyze 500 sperm per well without the need of a technician individually scoring each test in real time using phase contrast microscopy. This system is being used to provide a way to let the fixed stained sperm settle into the wells, such that both accelerated decondensation (5 min time point) and delayed decondensation (15 min time point) may be determined.

Fixation and staining has been optimized, as well as the time that the sperm must be put into the well to settle into the live cell array so that a maximum number of sperm that are individual and non-clumped can be analyzed by an image analysis system. The results achieved with this protocol yield results that closely match the phase contrast results for the 15 min time point (SDD Test) where a delay in decondensation is examined. Phase contrast results at the 5 min time point (SDAD Test) will be further examined to determine a match of data/analysis when examining accelerated decondensation.

Sperm Prep: same as in the phase contrast approach to scoring.

Egg Extract: same as in the phase contrast approach to scoring.

In a standard 96 well plate, transfer 50 ul of egg extract into each well using a pipetteman with 8 pipette tips that fit into the 8 wells in each row of the 96 well plate, i.e., run 8 assays at a time. Add 4 ul of sperm at a concentration of 25,000 sperm per ul and mix well. Start the timer. After a 5 min incubation a 25 ul aliquot of the extract/sperm cocktail is placed in the next 8 wells of the 96 well plate, and 1 ul of Hoescht 33258 stain (1 ul of stock Hoescht 33258 stain in 1 ml of water; 1:1,000 dilution) is added to each well and fixation solution is added in 5 μl aliquots per well (5 times) mixing the mixture in the well after each addition of fixative. The fixation solution is made by mixing a EM Grade paraformaldehyde, 16% w/v, Distilled Water, 100% v/v mix 1:1 with Phosphate Buffered Saline (PBS). The 50 ul of fixed stained sperm is then transferred into the 8 wells of the 96 well plate with the microwells at the bottom, into which the sperm will settle.

At the 10 min time point, 1 μl of 10% EtOH is added to the extract sperm incubation mixture. After incubating the sperm in the egg extract for 17 minutes, 1 ul of Hoescht 33258 stain (described above) is added to each of the 8 wells, and the fixation process is performed as described above. The 50 μl of fixed stained sperm is then transferred into the 8 wells of the 96 well plate with the microwells at the bottom, into which the sperm will settle.

This process will be repeated for groups of 8 patient samples until the 96 well plate is filled. The plate will then be placed into a refrigerator for analysis the next day.

Example 5

Manual Scoring of the Sperm DNA Accelerated Decondensation (SDAD) Test, and the Sperm DNA Decondensation (SDD™) Test Using Phase Contrast Microscopy For both the SDAD, and SDD Tests:

Semen: aliquots will be kept in the refrigerator at 2-8° C., until shipped cold by packing with a coolpak provided with shipping supplies. Specimens must be sent no later than 9 days after sample collection, and must be shipped on Monday, Tuesday, Wednesday or Thursday so they will not arrive on the weekend. The samples will be analyzed in the SDAD and/or the SDD Tests within 14 days of sample collection. Any sample arriving such that the sample can not be examined within the 14 day QC window will be rejected, and another sample requested.

Egg Extracts: Female *Xenopus Laevis* Oocyte positive frogs are maintained and the frog egg extracts produced as described in the attached Brown et. al. papers (1992, 1995). After preparing a frog egg extract Lot using a minimum of 15 frogs to provide eggs, the extract is immediately snap, deep-frozen as 30 ul drops in liquid $N_2$ (LN) that are transferred into cryo-vials that are kept in LN until thawed for use in performing the SDAD and SDD Tests. This frog egg extract will be used to induce the sperm DNA decondensation, mimicking the event after sperm entry into the oocyte.

The SDAD and SDD tests: About two million sperm per sample are washed and permeablized as described in the Brown et. al. papers (1992, 1995). After four extensive washes with special buffers, sperm are treated with a buffer containing dithiothreitol (DTT). The DTT-treated sperm are then incubated with frog egg extract to induce sperm DNA decondensation.

SDAD: After a 5 min incubation in egg extract, an aliquot of the sperm/egg extract mixture is placed on a glass slide and a cover slip is placed on top of the mixture. Approximately 50-75 sperm are scored in real time during a 5 min period of time, and the percentage of fully decondensed sperm is determined using phase contrast microscopy. The percentage of sperm fully decondensed is recorded. The raw data is normalized with a negative control (normal male as described below) decondensation value yielding the reportable value that is the percentage of the control sperm that have fully decondensed at 5 min. Any value less than 120% of the control is considered normal. Greater than 120% of the control is considered abnormal, and patients with such scores have a poor chance of having a successful ICSI attempt at pregnancy. This value is based on the results shown in FIG. 8.

SDD: After a 15 min incubation in egg extract, an aliquot of the sperm/egg extract mixture is placed on a glass slide and a cover slip is placed on top of the mixture. Approximately 50-75 sperm are scored in real time during a 5 minute period of time, and the percentage of fully decondensed sperm is determined using phase contrast microscopy. The percentage of sperm fully decondensed is recorded. The raw data is normalized with a negative control (normal male as described below) decondensation value yielding the reportable value that is the percentage of the control sperm that have fully decondensed at 15 minutes. Any score less than 80% of the control is considered an abnormal score. Such individuals have a poor chance of success in IUI or IVF-ET attempts at pregnancy. However, an abnormal SDD Test score cannot predict whether a patient will be successful in an ICSI attempt at pregnancy.

For both the SDAD and SDD Tests, in each test, one negative control and one positive control are run in parallel with the patient study samples. The negative control specimen is from a male who has produced 3 ejaculates that have normal decondensation at 15 min (typically 96±2 percent SD). Frozen donor sperm from a sperm bank can also be used, but the preferred negative control sample is an ejaculate kept at 4° C. for up to a month and used whenever needed during its 1 month shelf life. This control serves as a negative control when used in performing both the SDAD and SDD Test protocol. Positive controls (sperm that fails in the SDD Test) are routinely identified. Aliquots of these samples will be maintained for use as our positive control. The same protocol will be followed for the SDAD Test when it is offered commercially.

Example 6

Automated Scoring Process Data

The present example demonstrates the clinical relationship of results obtained using the Phase Contrast and the Florescent Image Analyses methods in using the SDAD assay. The present example also describes the equipment and presents clinical data in the form of captured images, and demonstrates the strong correlation, and hence predictive clinical value, between the Phase Contrast and Florescent Image Analysis as tools in monitoring and screening a human sperm sample.

Hardware and Software

MetaMorph Premier Acquisition system including workstation and hardware control capabilities for motorized microscope components, stage, camera, shutters as well as additional capabilities that can be used for future hardware integration.

Premier Off-line with LiveCell Array analysis drop-in for image processing. Hardware integration.

CoolSnap HQII scientific-grade digital camera and driver.

Motorized XY stage for Olympus IX71 microscope with controller, joystick and universal sample holder. Focus drive system to motorize control of IX71 microscope's fine focus.

Prior NanoScanZ 200 um Piezo Stage System. Includes sample holders for slides, dishes and microplates and DAQ Board For Piezo drive integration.

Uniblitz shutters for transmitted and fluorescent light paths with controller.

A 96 well plate with etched glass at the bottom of each well with a transparent array of micron-sized wells, with sperm analysis via image analysis software and hardware as one application.

A IX71 Olympus Inverted microscope with the filter system and a lwd 40× objective for fluorescence analysis of Hoescht 33258 stained sperm. Intercept: −2.66

TABLE 3

SDD TEST: % fully decondensed sperm DNA at 15 min

| Sample | Phase Contrast Real time | Fluorescence Image Analysis Auto Focus |
|---|---|---|
| 1 | 93.3 | 90 |
| 2 | 57.8 | 63 |
| 3 | 96.4 | 95.2 |
| 4 | 44.8 | 38.9 |
| 5 | 83.3 | 76.6 |
| 6 | 92.3 | 93.2 |
| 7 | 100 | 100 |
| 8 | 94.4 | 93.9 |

Slope: 1.0147
Correlation coefficient: 0.9831

The automated scoring approach yields the same results as the laborious manual scoring approach (See Table 3).

Example 7

Automation of the Sperm Processing for use in the SDAD and SDD Tests

This procedure will replace the manual protocol as described above. All the test steps will be done automatically by a liquid handling robotics from the first exposure of sperm to any reagent in the test itself to the fixation, so that no operator's action will be necessary. At the end of this process, the operator could transfer the plate to the refrigerator or to the automated scoring system described above.

Automated Performance of the Test Procedure

The present example describes the protocol performed by the liquid handling robotics that mimics the manual operation. The present example also describes the equipment needed for this procedure, and provides a comparison between a test result run manually and one run on the automated system, on the same specimen(s). The equipment is basically a liquid handling robotics that can handle the following functions:

Sample cells from a mixture of sperm at a pre-set concentration (eg. ten million sperm per milliliter), and set in an empty plate in which the assay is to be conducted (the assay plate).

Aliquot other solutions from a stock test tube, and delivering them to the assay plate.

Mix the sperm after any reagent addition, and before any aliquot removal from the assay plate.

Maintain the assay plate and the reagents' vessels in various desired temperature(s).

Mimicking the various steps in the manual process can then be done as in the example protocol as follows. However, this procedure is one example, but an automated approach is not limited to using the same concentrations, incubation times or steps as below. Thus, some steps may be performed in a different order, or perhaps eliminated altogether dependent on the particular conditions, etc., under consideration when running a particular sample batch, or dependent upon what materials are most readily available or convenient.

Aliquot a small volume of sperm suspension at a preset concentration in NIM;

Add a small volume of concentrated Lysolecithin (permeabilization) and mix Wait 5 minutes;

Add a high concentration of BSA to scavenge the Lysolecithin, and mix;

Move to 4° C.;

Add a small volume of highly concentrated DTT;

Incubate one hr at 4° C.;

Add diluting/washing buffer (XEIM) and mix;

Withdraw a certain volume;

Add similar volume of XEIM to replace the withdrawn volume, and mix;

Repeat the previous step to bring down the total cell numbers to be similar to the earlier developed manual method;

Add ice cold frog egg extract, and mix Incubate for 5 min (SDAD) or 15 min (SDD);

Add Hoechst 33258 fluorescent dye in a few microliter volume, to stain DNA;

Add Para formaldehyde fixative in several rounds of addition and mixing; and

Mix well and transfer entire volume to bottom-etched scoring plate.

Example 8

An Advanced Sperm Panel that Includes an SDAD Test, Lipid Peroxidation Test, and Sperm Early DNA Synthesis (SEDS) Test to Identify Patients not to be Directed to ICSI The present example is provided to demonstrate the utility of the 5-minute time point SDAD Test; in addition to new modifications to the HSAA methods described in U.S. Pat. Nos. 5,358,847, 5,770,363 and 5,919,621, and the Sperm Early DNA Synthesis (SEDS) Test, in identifying patients having sperm DNA damage resulting from exposure to ROS. The ROS damage of the sperm membrane will be confirmed by the use of a Lipid Peroxidation Test of the patient's sperm. To determine if the membrane damage is severe enough to allow for ROS damage to the sperm DNA, the SEDS Test will be used.

The SDAD Test is Described in Example 1

In vitro oxidative stress exposure; human sperm from a fertile male were exposed to increasing hydrogen peroxide ($H_2O_2$) concentrations (0, 10, 50 and 100 μM), and incubated at 37° C., for 15 min and 1 hr.

Lipid peroxidation (LPO) Test and HSAA responses were analyzed in each treatment to determine the effect(s) of $H_2O_2$ concentration and time exposure on human sperm activation responses.

Hydrogen Peroxide Dose-Response

Sperm preparation and oxidative treatments:

Semen ejaculate was collected in a sterile jar by masturbation after 3-5 days of sexual abstinence from fertile males who had previously been shown to produce sperm that responded normally in the HSAA. Sperm was isolated from the seminal plasma as previously described in Brown et al. 1995. The sperm pellet was resuspended in phosphate buffered saline (PBS), pH=7.4, and divided into 4 aliquots. Each aliquot (equal sperm concentrations) was incubated at 37° C. in PBS with $H_2O_2$ concentrations of 0, 10, 50, and 100 μM for 15 min and 1 hr. All aliquots were divided into 2 portions. One portion was used to determine LPO.

The remaining portion was centrifuged at 1500 g for 15 min at room temperature. The pellet was analyzed in the HSAA.

Lipid Peroxidation Measurements

Aliquots of sperm previously exposed to increasing concentrations of $H_2O_2$ designed to determine LPO were centrifuged at 10,000 g for 10 min at 4° C., the supernatants were placed on ice, and the sperm pellets (approximately 20 million cells) were sonicated using an XL Ultrasonic Cell Disruptor (Microson). Sonication was performed in 3 cycles consisting of 5 sec of sonication followed by 30 sec of incubation on ice. Following sonification, samples were centrifuged at 10,000 g for 10 min. An Oxford Biomedical Research Kit Fr 12 was used to determine LPO (MDA+Hydroxyalkenal concentrations) in the supernatants and the sonicated sperm. This technique is based on the reaction of a chromogenic reagent, N-methyl-2 phenylindole, with MDA and 4-hydroxyalkenals at 45° C. One molecule of either MDA or 4-hydroxyalkenal reacts with 2 molecules of N-methyl-2 phenylindole to produce a stable chromophore that can be quantified at 586 nm.

Cellular Events of Human Sperm Activation

A. Nuclear Decondensation and Recondensation

Figure 1:
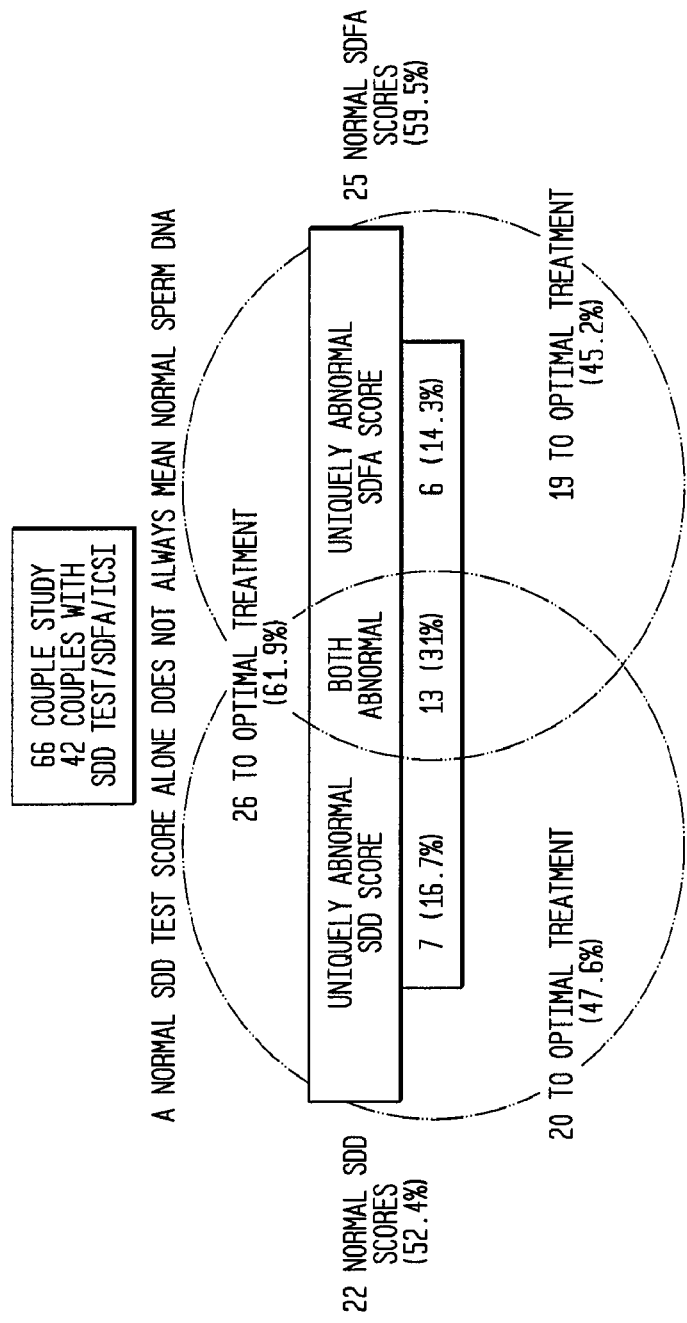
FIG. 1: A graphic showing tests to maximize patients going directly to ICSI
Figure 2:
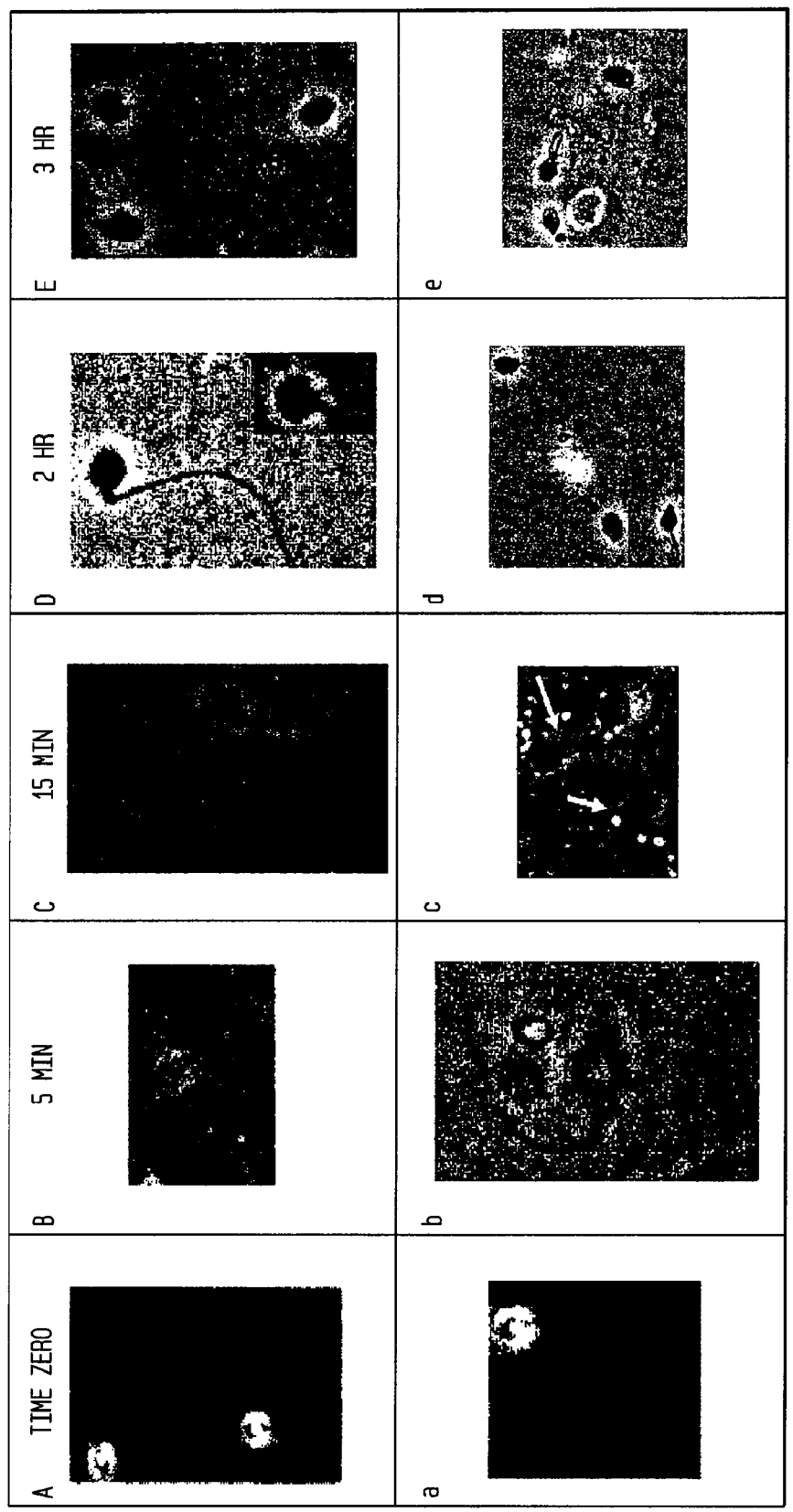
FIG. 2: The effects of oxidative stress on human sperm activation. Pictorial representation of the Effects of $H_2O_2$ on human sperm activation: Sperm samples were treated with different concentrations of $H_2O_2$ and analyzed in the HSAA as described in Materials and Methods section. All sperm were photographed using phase contrast microscopy, a 60× objective, and were printed at the same magnification. (A-E) HSAA normal responses in untreated control sperm incubated in egg extract. (a-e) Sperm exposed to 100 μM $H_2O_2$ for 1 hr and then incubated in egg extract. The arrows point to examples of abnormal sperm activation responses. Bar represents 10 μm.

These results indicate that $H_2O_2$ concentration (50 and 100 μM) and time exposure are the main factors that induced accelerated decondensation responses including: 1) the unique observation of early recondensation, and 2) the novel phenomenon of hyperdecondensation (FIG. 2).

B. Nuclear Recondensation

Sperm chromatin recondensation after a 2 and 3 hr incubation in egg extract

There were no differences in recondensation observed at the 2 and 3 hr incubation times in egg extract so the results were combined. In addition, spermatozoa have already advanced beyond decondensation by two and three hours. For this reason, fully decondensed, partially decondensed, and non-decondensed sperm were not observed. No sperm were hyper-decondensed in the control and 10 μM $H_2O_2$-treated sperm. Hyper-decondensation occurred in 35.2% and 45±2% of the sperm treated with 50 and 100 μM $H_2O_2$, respectively (15 min exposure) Hyper-decondensed sperm occurred in 30±2% and 45±3% of the sperm treated with 50 and 100 μM $H_2O_2$, respectively (1 hr exposure). Recondensed sperm were observed in 98±2% of both the control, and 10 μM $H_2O_2$-treated sperm (15 min and 1 hr exposure). Recondensation occurred in 66±2.3% and 57±2% of the sperm exposed to 50 and 100 μM $H_2O_2$ respectively (15 min exposure). Recondensation occurred in 70+3% and 54+2% of the sperm exposed to 50 and 100 μM $H_2O_2$ for 1 hr, respectively. Examples of hyperdecondensation, accelerated decondensation, and recondensation are shown in FIG. 2.

These results indicate that 1) nuclear recondensation is $H_2O_2$ concentration and time exposure dependent, and 2) oxidative stress promotes nuclear arrest in the hyperdecondensed state.

C. DNA Synthesis ($^3$H-TTP Incorporation)

Figure 3:
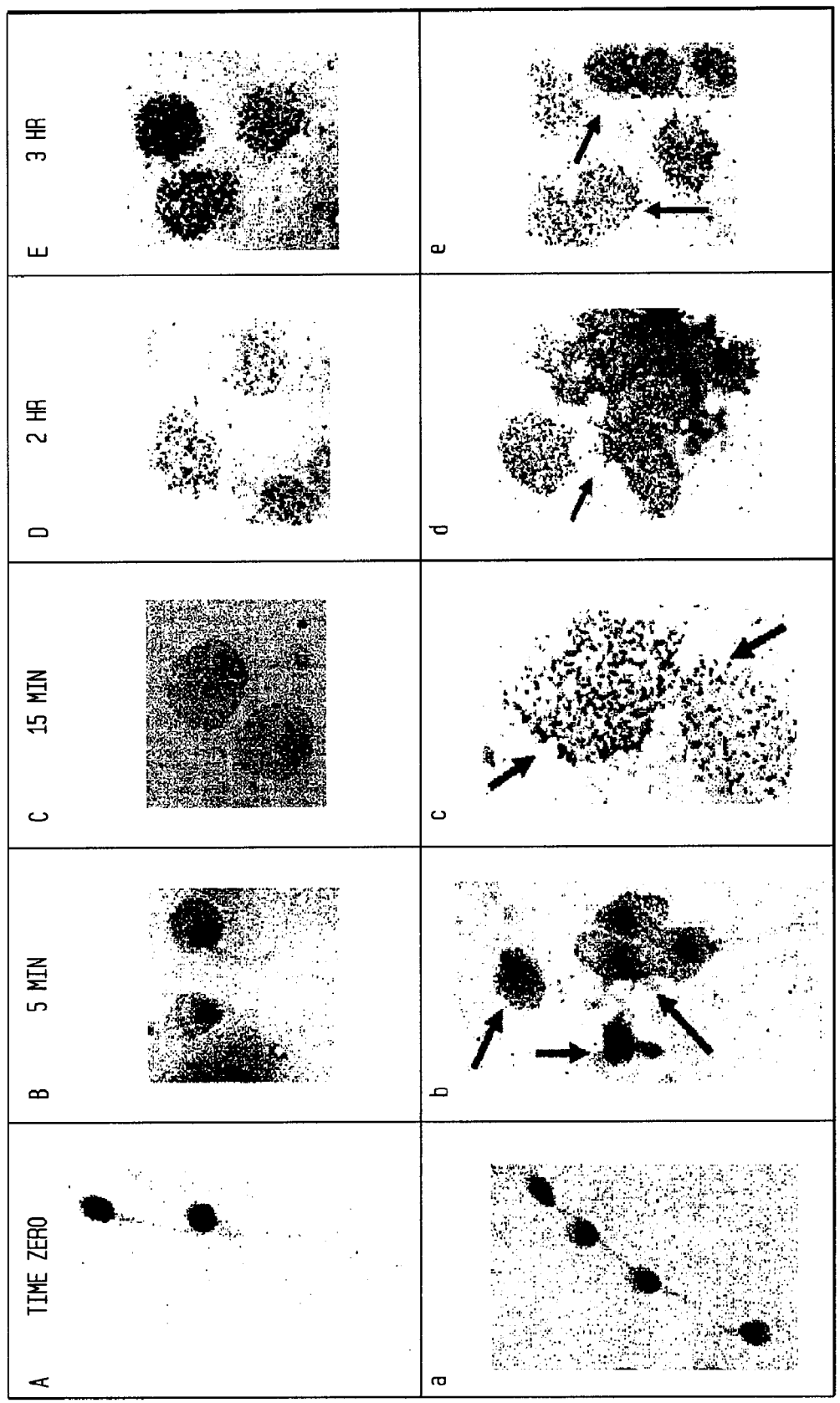
FIG. 3: HSAA—The effect of oxidative stress on DNA synthesis. Pictorial representation of autoradiographs of control untreated sperm (A-E) and sperm exposed to 100 μM $H_2O_2$ for 1 hr (a-e) assayed in the HSAA in the presence of $^3$H-TTP. All the pictures were photographed using bright microscopy 60× objective. The black bar represents 10 μM, and black arrows point to abnormal sperm activation. All pictures were printed at the same magnification.

$^3$H-TTP incorporation into sperm DNA after a 5 min incubation in egg extract (FIG. 3).

No sperm were positive for $^3$H-TTP incorporation in the control and 10 μM $H_2O_2$-treated sperm after a 15 min extract incubation. (FIG. 3). Sperm classified as having medium $^3$H-TTP labeling were observed in 18±3.5% and 36±3% of the 50 μM $H_2O_2$-treated sperm after a 15 min and 1 hr exposure, respectively. Approximately 25±5% and 48±2% of the 100 μM $H_2O_2$-treated sperm had medium $^3$H-TTP labeling after a 15 min and 1 hr exposure, respectively. Sperm heavily labeled by $^3$H-TTP were observed in 10±3.5% and 28±2% of sperm exposed to 50 μM $H_2O_2$ and 15±5% and 31±3% of the sperm exposed to 100 μM $H_2O_2$ for 15 and 1 hr, respectively.

Approximately 28±4% of the sperm were fully decondensed in both the control and 10 μM $H_2O_2$-treated sperm (15 min exposure) and 30±6% at 1 hr exposure. Fully decondensed sperm were observed in 43.3±3.7% and 46.6±6% of the 50 μM $H_2O_2$ treated sperm after a 15 min and 1 hr exposure, respectively. Fully decondensed sperm were observed in 56.6±4.7% and 64.5±4.5% of the 100 μM $H_2O_2$-treated sperm after a 15 min and 1 hr exposure, respectively. Approximately 30% of both the control, and 10 μM $H_2O_2$-treated sperm were partially decondensed (15 min and 1 hr exposures). Approximately 1% of both the 50 and 100 μM $H_2O_2$-treated sperm (15 min and 1 h exposures) were partially decondensed. Approximately 35-40% of both the control and the 10 μM $H_2O_2$-treated sperm (15 min and 1 hr exposures) showed no decondensation. Non-decondensed sperm were observed in 15±3 and 18±4% of the sperm treated with 50 μM and 10+2% of sperm treated with 100 μM $H_2O_2$ (15 min and 1 hr exposures), respectively. No sperm were hyperdecondensed in the control and 10 μM $H_2O_2$-treated sperm.

Hyperdecondensation occurred in 38.4%, and 26% of the sperm treated with 50 and 100 μM $H_2O_2$, respectively, after a 15 min exposure. Hyperdecondensed sperm occurred in 31±4% and 11±4% of the sperm after a 1 hr exposure. No recondensed sperm were observed in control, 10 μM $H_2O_2$-treated sperm (15 min and 1 hr exposures), and 50 μM $H_2O_2$-treated sperm for 15 min exposures. Recondensation occurred in 8±2% of the sperm exposed to 100 μM $H_2O_2$ for 15 min. Recondensation occurred in 5±3% and 15±2% of the sperm exposed to 50 and 100 μM $H_2O_2$ for 1 hr, respectively.

The oxidative stress that resulted in the above abnormal in vitro sperm activation in the $H_2O_2$ treated sperm, may be the result of a combined detrimental effect on: 1) the plasma membrane, and 2) DNA integrity. Possibly, the hyperdecondensation effect can be explained by the massive influx of the activation factors contained in the extract, through the leaky membrane. Damage to the plasma membrane, when lipid peroxidation of polyunsaturated fatty acids occurred, results in an increase in the permeability of the membranes. Also, the 'oxidative chromatin pre-relaxation' may accelerate sperm nuclear decondensation (Ollero M et al. 2000; Kemal Duru N et al. 2000; Saleh R A et al. 2002). These findings are in agreement with the results of Brown, et al., 1987 who showed that nuclear factors contained in the egg extract regulate sperm decondensation. In an in vitro decondensation kinetics study, sperm was incubated in an active fraction of proteins isolated from the frog egg extract that contained a 70-fold enrichment of partially purified decondensation activation factors. Full decondensation of the sperm nuclei occurred within 5 minutes, and no recondensation was observed, indicating that the recondensation proteins were removed or inactivated during the purification of the decondensation proteins (Brown D B et al. 1987; Brown D B et al. 1991).

Some abnormal sperm decondensation responses are believed to be a result of exposure to reproductive toxicants that directly affect the chromatin such that there is a delay or an enhancement of in vitro decondensation, depending upon the type of exposure. For example, exposure to alkylating agents causes a delayed decondensation (Perreault S et al. 1987 et al. Sawyer D et al. 1995; Sawyer et al. 1998). Exposure to ROS induced an increase in the kinetics of decondensation (accelerated decondensation). Other abnormal responses such as an increase in the recondensation kinetics, may be a result in altered quantities, or enzyme activity of activation factors related to the decondensation/recondensation processes, again due to the damaged membrane (Brown D B et al. 1987; Brown D B et al. 1991; Philpott A et al. 1991; Brown et al. 1992; Philpott A et al. 1992; Brown D B et al. 1995; Matsumoto K et al. 1999; Sawyer D et al. 2000).

This study supports that high levels of ROS (50 to 100 µM $H_2O_2$) results in oxidative stress. The oxidative stress results in membrane and DNA damage, translates to sperm DNA accelerated decondensation (SDAD) when such sperm is analyzed at the 5 minute time point.

Results

Lipid Peroxidation Measurements

To determine the effect of increasing $H_2O_2$ concentrations on the production of LPO, a spectrophotometric assay was used to measure the amount of MDA and hydroxyalkenals in sperm treated with 0, 10, 50 and 100 µM hydrogen peroxide ($H_2O_2$) for 15 min and 1 hr. The means were significantly different in 50 and 100 µM $H_2O_2$-treated sperm (15 min), and 10, 50 and 100 µM $H_2O_2$-treated sperm (1 hr), when compared to the untreated control sperm. These results indicate that lipid peroxidation is concentration- and exposure time-dependent.

Effect of Oxidative Stress on Human Sperm Activation

Sperm chromatin decondensation and nuclear recondensation were evaluated in sperm exposed to increasing concentrations of $H_2O_2$ for 15 min and 1 hr using the HSAA. Sperm were analyzed at different incubation times in the egg extract using the image analysis Methamorph software system. The sperm nuclear activation was scored in 5 categories: 1) full decondensation: sperm diameter 25-30 µm, 2) partial decondensation: sperm diameter<25 µm, 3) non-decondensed, 4) hyperdecondensed: sperm diameter>(25-30 µm), and full recondensation.

Cellular Events of Human Sperm Activation

A. Nuclear Decondensation and Recondensation

Sperm chromatin decondensation and recondensation after a 5 min incubation in egg extract.

Approximately 28±4% of the sperm were fully decondensed in both the control and 10 µM $H_2O_2$-treated sperm (15 min exposure) and 30±6% (1 hr exposure). Fully decondensed sperm were observed in 43.3±3.7% and 46.6±6% of the 50 µM $H_2O_2$ treated sperm after a 15 min and 1 hr exposure, respectively. Fully decondensed sperm were observed in 56.6±4.7% and 64.5±4.5% of the 100 µM $H_2O_2$-treated sperm after a 15 min and 1 hr exposure, respectively. Approximately 30% of both the control, and 10 µM $H_2O_2$-treated sperm were partially decondensed (15 min and 1 hr exposures). Approximately 1% of both the 50 and 100 µM $H_2O_2$-treated sperm (15 min and 1 hr exposures) were partially decondensed. Approximately 35-40% of both the control and the 10 µM $H_2O_2$-treated sperm (15 min and 1 hr exposures) showed no decondensation. Non-decondensed sperm were observed in 15±3 and 18±4% of the sperm treated with 50 µM $H_2O_2$ and 10±2% of sperm treated with 100 µM $H_2O_2$ (15 min and 1 hr exposures), respectively. No sperm were hyperdecondensed in the control and 10 µM $H_2O_2$-treated sperm. Hyperdecondensation occurred in 38.4%, and 26% of the sperm treated with 50 and 100 µM $H_2O_2$, respectively, after a 15 min exposure (FIG. 3a). Hyperdecondensed sperm occurred in 31±4% and 11±4% of the sperm after a 1 hr exposure. No recondensed sperm were observed in control, 10 µM $H_2O_2$-treated sperm (15 min and 1 hr exposures), and 50 µM $H_2O_2$-treated sperm for 15 min exposure. Recondensation occurred in 8±2% of the sperm exposed to 100 µM $H_2O_2$ for 15 min. Recondensation occurred in 5±3% and 15±2% of the sperm exposed to 50 and 100 µM $H_2O_2$ for 1 hr.

Sperm Chromatin Decondensation and Recondensation after a 15 Min Incubation in Egg Extract.

Approximately 94% of the sperm were fully decondensed in both the control and 10 µM $H_2O_2$-treated sperm (15 min and 1 hr exposures). Fully decondensed sperm were observed in 53±3% and 58±2% of the 50 µM $H_2O_2$-treated sperm after a 15 min and 1 hr exposure, respectively. Fully decondensed sperm were observed in 48±1.5% and 47±2% of the 100 µM $H_2O_2$-treated sperm after a 15 min and 1 hr exposure, respectively. Approximately 5% of the sperm were non-decondensed in the control and the 10 µM treatment at both time points. However, no sperm were non-decondensed for any other concentrations at any of the time points. No sperm were hyperdecondensed in the control and 10 µM $H_2O_2$-treated sperm. Hyperdecondensation occurred in 45.2% and 37% of the sperm treated with 50 and 100 µM $H_2O_2$, respectively. Hyperdecondensed sperm occurred in 30±2% and 33±3.5% of the sperm (1 hr exposure. No recondensed sperm were observed in control, 10 and 50 µM $H_2O_2$-treated sperm (15 min exposure). Recondensation occurred in 15±3% of the sperm exposed to 100 µM $H_2O_2$ (15 min exposure). Recondensation occurred in 10±2% and 20±2% of the sperm exposed to 50 and 100 µM $H_2O_2$ for 1 hr.

No sperm were positive for $^3$H-TTP incorporation in the control and 10 µM $H_2O_2$-treated sperm after 15 min and 1 hr exposures. Sperm having medium labeling were observed in approximately 20±3% and 30±10% of sperm exposed to 50 and 100 µM $H_2O_2$ for 15 minutes, respectively. Approximately 21±5%, 37±9% of the sperm exposed for 1 hr to 50 and 100 µM $H_2O_2$, had medium labeling, respectively. Sperm heavily labeled by $^3$H-TTP incorporation were observed in 10±2% and 17.5±7.5% of sperm exposed to 50 µM $H_2O_2$ and 50±5% and 45±9% of sperm exposed to 100 µM $H_2O_2$ at 15 min and 1 hr, respectively.

$^3$H-TTP incorporation into sperm DNA after a 2 hr incubation in egg extract.

Sperm with medium labeling were observed in approximately 14.5±4% and 43.5±5% of sperm exposed to 50 and 100 µM $H_2O_2$ for 15 min and 1 hr, respectively. Approximately 36±2% and 28.5±2.5% of the sperm exposed for 1 hr to 50 and 100 µM $H_2O_2$, had medium labeling, respectively. Sperm heavily labeled by $^3$H-TTP incorporation were found in 99±1% of the sperm in the control and 10 µM $H_2O_2$-treatments at both 15 min and 1 hr exposures (FIGS. 6a and 6b). Sperm with heavy labeling were observed in 85±5% and 56.5±3% of the sperm exposed to 50 µM $H_2O_2$ for 15 min and 1 hr, respectively. Approximately 64±2% and 71±3% of the sperm exposed to 100 µM $H_2O_2$ for 15 min and 1 hr, showed heavy labeling, respectively.

$^3$H-TTP incorporation into sperm DNA after a 3 hr incubation in egg extract. Sperm with medium labeling were observed in approximately 16.5±2% and 14.5±3% of sperm exposed to 50 and 100 µM $H_2O_2$ for 15 minutes, respectively. Approximately 25±3% and 40±4% of the sperm exposed for 1 hr to 50 and 100 µM $H_2O_2$, had medium labeling respectively. Heavily labeled sperm were found in 98±2% of the control and 10 µM $H_2O_2$-treated sperm after 15 min and 1 hr exposures. Sperm with heavy labeling were observed in approximately 78±6% of the sperm exposed to 50 µM $H_2O_2$ and 85±5% of the sperm exposed to 100 µM $H_2O_2$ for 15 min. Approximately 75±3% of the sperm exposed to 50 µM $H_2O_2$ and 60±4% of the sperm exposed to 100 µM $H_2O_2$ for 1 hour, had heavy labeling.

These DNA synthesis results indicate that: 1) oxidative stress induces early DNA synthesis ($^3$H-TTP-incorporation) during nuclear decondensation after a 5 and 15 min incubation in the frog egg extract, 2) early DNA synthesis was $H_2O_2$ concentration and exposure time dependent, 3) abnormal DNA synthesis was observed in the 50 and 100 µM $H_2O_2$ treated sperm after a 2 and 3 hr incubation in the egg extract, such treated sperm had a significant decrease in heavily labeled nuclei that was again concentration and exposure time dependent.

The results obtained in this study demonstrate that the concentration of hydrogen peroxide and exposure time were the main factors that induced lipid peroxidation that correlated with abnormal sperm activation responses. Abnormal responses included: a) decondensation, b) an increased number of sperm with premature, fully decondensed nuclei, c) the unique observation of early recondensation, and the novel phenomenon of hyperdecondensation after a 5 and 15 min incubation in egg extract. Oxidative stress promoted abnormal recondensation and nuclear arrest in the hyperdecondensed state in 33-42% of the sperm nuclei observed in 50 and 100 µM $H_2O_2$-treated sperm after a 3 hr incubation in the egg extract. Oxidative stress induced early DNA synthesis activity during nuclear decondensation at 5 and 15 min. The DNA synthesis activity was ROS concentration- and exposure time-dependent.

The oxidative stress that resulted in the above abnormal in vitro sperm activation in the $H_2O_2$ treated sperm, is a combined detrimental effect on: 1) the plasma membrane, and 2) DNA integrity. Possibly, the hyperdecondensation effect can be explained by the massive influx of the activation factors contained in the extract, through the leaky membrane. Also, the 'oxidative chromatin pre-relaxation may accelerate sperm nuclear decondensation (Ollero M et al. (2000)); Kemal Duru N et al. (2000); Saleh R A et al. (2002).

In an in vitro decondensation kinetics study, sperm were incubated in an active fraction of proteins isolated from the frog egg extract that contained a 70-fold enrichment of partially purified decondensation activation factors. Full decondensation occurred within 5 minutes, and no recondensation was observed, indicating that the recondensation proteins were removed or inactivated during the purification of the decondensation proteins (Brown D B et al. (1987); Brown D B et al. (1991)).

Some abnormal sperm decondensation responses are believed to be a result of exposure to reproductive toxicants that directly affect the chromatin such that there is a delay or an enhancement of in vitro decondensation, depending upon the type of exposure. For example, exposure to alkylating agents causes a delayed decondensation (Perreault S et al. (1987), Sawyer D et al. (1995); Sawyer et al. (1998)), while exposure to ROS induced an increase in the kinetics of decondensation. Other abnormal responses, such as an increase in the recondensation kinetics, may be a result in altered quantities, or enzyme activity of activation factors related to the decondensation/recondensation processes, again due to the damaged membrane (Brown D B et al. (1987); Brown D B et al. (1991); Philpott A et al. (1991); Brown et al. (1992); Philpott A et al. (1992); Brown D B et al. (1995); Matsumoto K et al. (1999); Sawyer D et al. (2000)).

The autoradiography results in the present study indicate that both the control (untreated) and sperm exposed to 10 µM $H_2O_2$ for 15 min and 1 hr had no incorporation of $^3$H-TTP after 5 and 15 min incubations in the egg extract, and normal $^3$H-TTP incorporation after 2 and 3 hr incubations in frog egg extract. These results are in agreement with previous in vitro studies, which have defined the standard values of $^3$H-TTP incorporation in fertile males that responded normally in the HSAA (Perreault S et al. (1987); Brown D B et al. (1992); Sawyer D et al. (1995); Brown D B; et al. (987), Brown D B et al. (1995); Sawyer D et al. (1998); Sawyer D et al. (2000)). In agreement with the previous studies, a) No $^3$H-TTP incorporation "unlabeled" during sperm chromatin decondensation was observed at the 5 and 15 min in egg extract, and b) approximately 97 to 99% of the sperm population incorporated $^3$H-TTP ("heavy label"; more than 25 black granules per sperm nucleus) after 2 and/or 3 hr incubation in the egg extract. However, the $^3$H-TTP incorporation results of sperm exposed to 50 and 100 µM $H_2O_2$ for 15 min and 1 hr, show that sperm had abnormal $^3$H-TTP incorporation including: a) early DNA synthesis after a 5 and 15 min incubation in the egg extract, and b) increase in the number of sperm positive for medium label after 2 and 3 hr incubations in the egg extract. The abnormal $^3$H-TTP incorporation was $H_2O_2$ concentration and exposure time dependent.

In vitro studies indicate that chromatin decondensation is required for DNA synthesis, specifically for the formation and maturation of the male pronucleus. DNA synthesis is engineered totally by factors present in the egg extract; one of these factors is the enzyme DNA polymerase □.

In the untreated control sperm, and sperm exposed to 10 µM $H_2O_2$ for 15 min and 1 hr, no $^3$H-TPP incorporation was observed. After a 1 hr incubation in egg extract, all sperm are synthesizing DNA. This DNA synthesis is believed to be semi-conservative DNA synthesis typical for S phase of the cell cycle (Brown D B et al. (1987)), Mazia D (1963)).

The early DNA synthesis activity observed in sperm exposed to 50 and 100 µM $H_2O_2$ for 15 min and 1 hr suggests that the DNA synthesis observed is repair DNA synthesis of the ROS damaged DNA. As sperm does not have DNA repair capacity (Ramos et al. (2001)), the DNA repair activity must be provided by egg cytoplasm. DNA repair activity has been found to be dependent upon oocyte cytoplasmic factors (Baarends et al. (2001)); Ochsendorft (1999)).

The early DNA synthesis is believed to be DNA repair. These results are in agreement with Sawyer at al. (1995). The results of sperm exposed to hydroxylamine, a mono-functional DNA damaging agent, that were subsequently analyzed in the HSAA, indicate that the mutagen induces abnormal sperm activation responses that include minimal decondensation, and the early initiation of DNA synthesis. In this study, it is hypothesized that the damaged DNA, activated DNA repair machinery present in the frog egg extract, and thus resulted in an early onset of DNA synthesis (Zhi et al. (1997); Sawyer D et al. (2000)).

Since sperm does not have DNA repair capacity (Ramos L et al. (2001), the DNA repair activity must be provided by egg cytoplasm. DNA repair activity has been demonstrated in several mouse models for male infertility, and in biopsies taken from infertile males in which DNA integrity is compromised suggests that the repair of DNA-oxidative damage occurs between sperm decondensation and pronucleus formation, and that the DNA repair is dependent on oocyte cytoplasmic factors (Baarends et al., (2001), Ochsendorft F R (1999)). The autoradiography results in this present study are in agreement with the above observations.

The results indicate that $H_2O_2$ at 50 and 100 µM concentrations produced DNA damage that resulted in abnormal activation responses. Additional studies indicate that sperm exposed to endogenous ROS, or direct exposure to $H_2O_2$, resulted in a dose-dependent induction of high rates of DNA fragmentation. Such induction was significant at 200 µM concentrations of $H_2O_2$. The resulting DNA fragmentation was observed using the comet assay (Kemal Duru N et al. (2000)).

The base excision DNA repair pathway is used to repair DNA oxidative damage. In addition, DNA repair mechanisms have been involved not only in the repair of DNA damage in developing germ line cells, but also to enhance specialized gene expression during mammalian gametogenesis (Baarends W et al. (2001)).

This study supports that high levels of ROS (50 to 100 µM $H_2O_2$) results in oxidative stress. The oxidative stress results in membrane and DNA damage that translates to abnormal responses when such sperm is analyzed in the HSAA.

Patients identified as having accelerated DNA decondensation in the SDAD test should be tested for if this is a result of membrane damage (LPO Test) that is allowing the DNA to be exposed to ROS that is getting through the now leaky membrane. If this is the case, the SEDS Test will be positive indicating that DNA damage has occurred. The next example indicates a possible treatment for such patients, i.e., anti-oxidant therapy.

Example 9

Oxidative Stress: Protective Effects of 6-Hydroxy-2, 5,7,8-tetramethylchroman-. 2-carboxylic acid (Trolox) on Human Sperm Activation. Oxidative Stress: Protective Effects of 6-Hydroxy-2,5,7,8-tetramethylchroman-. 2-carboxylic acid (Trolox) on Human Sperm Activation Oxidative stress is a result of an imbalance caused by: 1] over production of reactive oxygen species (ROS), and/or 2] reduced scavenger capacity. Conditions such as inflammation and/or infection are known to produce ROS and can result in oxidative stress. High levels of ROS is believed to have detrimental effects on sperm function. When sperm from a fertile male was treated in vitro with ROS (50 and 100 µM $H_2O_2$), the ROS damaged sperm responded abnormally when analyzed in the human sperm activation assay (HSAA).

ROS generated by polymorphonuclear leukocytes (PMNL) results in an abnormal response of PMNL/ROS-exposed sperm when analyzed in the HSAA, and 2) Trolox, an antioxidant agent, ameliorates PMNL induced oxidative damage, thus resulting in a normal response when PMNL/ROS/Trolox-treated sperm are analyzed in the HSAA.
Design Comparative study of the effects of oxidative stress on sperm with or without an anti-oxidant treatment.
Materials and Methods PMNLs were isolated from blood of healthy donors by density gradient centrifugation. Activation and the number of peroxidase-positive leukocytes were determined using the Endtz test. Sperm from fertile males were isolated using percoll gradients (40 and 80%). Sperm from the 80% fraction was divided into 6 aliquots: 1) control non-treated sperm, 2) sperm treated with ROS inducer phorbol-12 myristate-13 acetate (PMA), 3) non-treated sperm with non-treated PMNL, 4) sperm with PMA treated PMNL, 5) sperm with PMA treated PMNL plus Trolox 40 µM, and 6) non-treated sperm plus Trolox 40 µM. Following an incubation period, sperm were evaluated for (A) sperm activation events in the HSAA, evaluating sperm activation events (decondensation, DNA synthesis, and recondensation) at 15 min, and 2 hr, and (B) determining ROS levels via nitroblue of tetrazolium (NBT) and spectrophotometry.
Results Sperm exposed to high levels of ROS generated by PMA-activated polymorphonuclear leukocytes (PMNL), had abnormal responses in the HSAA, including hyperdecondensation (sperm showing at least a 2 fold increase in size over that observed for typical fully decondensed sperm), an early onset of $^3$H-TTP incorporation, and an increase in the percentage of hyper-decondensed sperm that did not recondense (only 57% sperm had recondensed chromatin at the 2 hr time point). Sperm exposed to oxidative stress in the presence of Trolox, had improved responses in decondensation with no early $^3$H-TTP incorporation, with 78% of the sperm having recondensed chromatin at the 2 hr time point.

The abnormal HSAA responses of sperm exposed to oxidative stress generated by activated PMNL demonstrates that ROS-generating PMNL can induce detrimental effects on human sperm chromatin. The early onset of DNA synthesis and the hyperdecondensation may be explained by the damaged sperm activating DNA repair pathways when such sperm are incubated in the frog extract used when performing the HSAA. These adverse effects were partially reduced by incubating the sperm with Trolox, reducing oxidative damage that translated to a near-normal response of Trolox-treated sperm when they were analyzed in the HSAA.

Although this data is for sperm being damaged by in vitro ROS exposure, the expanded HSAA may be used in conjunction with the LPO Test to identify anti-oxidant cocktails to be used as an anti-oxidant therapy for patients having accelerated DNA decondensation that is a result of ROS damage.

Example 10

Use of the Sperm DNA Decondensation (SDD™) Test in Predicting Fertility Benefit from a Varicocelectomy The present example demonstrates the utility of the present invention as a diagnostic test for determining infertile males who can benefit from a varicocelectomy(VX).

The SDD Test has this capacity, as well as utility in monitoring improvement of sperm post-surgery to determine when a couple should resume ART attempts at pregnancy. The SDD Test assesses the decondensation human sperm activation event (nuclear swelling) by incubating permeabilized human sperm in frog egg extract and observing how a patient's sperm decondenses relative to a normal fertile male's sperm. Any score less than 80% of the control is considered abnormal. The resent example demonstrates:
1) Individuals with abnormal SDD Test scores and with a varicocele(s) confirmed by a urologist can benefit from a varicocelectomy, and
2) By monitoring the SDD Test scores beginning 3 months post-surgery, individuals with substantial improvement will have a higher live birth outcome either by natural conception, or the use of ART.
Design Retrospective, single center study
Materials and Methods Using medical records from 1 fertility practice, a retrospective chart review was performed on men sent to a urologist for varicocele evaluation because of an abnormal SDD Test score.
Results Nineteen males with abnormal SDD Test scores agreed to go to a urologist for further evaluation. Twelve of the 19 males were found to have varicocele(s). Nine males chose to have a VX, 3 males opted NOT to have the surgery. Of the 9 males who had the VX, 7 had repeat SDD Tests performed 3-5 months post-surgery. In all cases, substantial improvements in their SDD Test scores occurred. Two males had spontaneous conceptions (SC) and did not have a repeat SDD Test. One SC resulted in a live birth, the other spontaneously aborted at 6 weeks. Six of the 9 males with improved repeat scores fathered children either by natural conception (1) or by ART (3 singletons, 2 twins). One of the 7 males had a negative IVF. Thus, in the group who opted for the VX, 7 of 9 (78%) fathered children. No children (0%) were fathered by the 3 males who refused the VX.

These results demonstrate that the SDD Test can identify men with varicocele(s) who will have a fertility benefit from a varicocelectomy (p=0.045; Fisher Exact Test). The SDD Test may also be a useful marker of improved fertility potential of sperm after a varicocelectomy. Further clinical studies are needed to determine the SDD Test's utility for managing varicocele(s) and male infertility.

Age of Patients:

| Had Varicocelectomy | | Declined Varicocelectomy | |
| --- | --- | --- | --- |
| Female | Male | Female | Male |
| 29 | 32 | 29 | 29 |
| 37 | 40 | Opted to try for Spontaneous Conception | |
| 31 | 33 | 39 | 40 |
| 35 | 29 | (Opted for anti-oxidant therapy) | |
| 36 | 36 | 50 | 49 |
| 25 | 28 | (Opted for donor eggs) | |
| 36 | 38 | | |
| 36 | 36 | | |
| 32 | 48 | | |

Example 11

The Use of the Advanced Sperm Panel in Determining Patient Treatment

The present example demonstrates how an advanced sperm panel can be used to direct a couple to the most appropriate treatment(s). The panel includes, but is not limited too:

The SDAD Test, SDD Test, SDFA Test, LPO Test, SEDS Test, HSAA DNA Synthesis Test, and HSAA Recondensation Test.

If the SDAD Test is Abnormal, the LPO, SEDS Test, and HSAA DNA Synthesis Tests should be performed to confirm the infertility problem is related to ROS damage. If this is the case, the male should be put on an anti-oxidant therapy before this patients' specimen is used in performing any ART. Such patients should not be directed to ICSI unless their condition changes and in subsequent SDAD tests the SDAD test score provides a normal SDAD reading.

If the SDD Test and/or the SDFA scores are abnormal, such patients should be not use IUI or IVF, the patients should consider ICSI early on as the optimal ART procedure.

If the SDD Test is abnormal, the patient should be checked by a Urologist for varicocele(s). If a varicocele (s) is found, the patient should be offered a varicocelectomy. SDD Tests should be performed every three months post surgery until their score is normal. At this point if they don't have a natural conception, they should be directed to the appropriate ART based on the female's condition.

BIBLIOGRAPHY

The following references are specifically incorporated herein in their entirety by reference:

Brown, et al., "Use of *Xenopus laevis* Frog Egg Extract in Diagnosing Human Male Unexplained Infertility", The Yale Journal of Biology and Medicine 65 (1992), 29-38.

Brown, et al., "Some cases of human infertility are explained by abnormal in vitro human sperm activation", Fertility and Sterility, Vol. 64, No. 3, September 1995.

Evenson et al. (1980) (Science, 210:11 31-3).
Evenson et al. (1999) Human Reproduction, 14 (1039-49).
Sawyer, et al., "Altered Nuclear Activation Parameters of Rat Sperm Treated in Vitro with Chromatin-Damaging Agents", Toxicological Sciences 44, 52-62 (1998).
Sawyer, et al., "Diminished decondensation and DNA synthesis in activated sperm from rats treated with cyclophosphamide", Toxicology Letters 114 (2000) 19-26.
Sawyer, et al., "The Use of An In Vitro Sperm Activation Assay To Detect Chemically Induced Damage of Human Sperm Nuclei", Reproductive Toxicology, Vol. 9, No. 4, pp. 351-357, 1995.
Tirado, et al., "Comparison of lipid peroxidation and sperm function after isolating sperm using a density gradients."
Tirado, et al., "Oxidative stress: Protective effects of 6-Hydroxy-2,5,7,8-tetramethylchroman-. 2-carboxylic acid (Trolox) on human sperm activation", presented at the combined ASRM/CFAS meeting in Montreal, Quebec, Oct. 15-19, 2005.
Tirado, et al., "Effects of Oxidative Stress on Human Sperm Activation", presented at the 2003 ASRM meeting held in San Antonio, Tex.
Abou-Haila A, et al. Arch of Biochem and Bioph 2000; (379): 173-182.
Aitken R J., et al. Fertil Steril 1990; (54): 701-707.
Aitken R J., et al. Am J Reprod Immunol 1996; (35): 541-551.
Aitken R J; Vernet P. J Reprod Fertil Suppl. 1998; (53):109-118.
Aitken J. The Amoroso Lecture. The human spermatozoon: a cell in crisis? J Reprod Fertil. 1999; (115): 1-7.
Alvarez J G, et al. Fertil Steril 2004; 81 (3):712-713.
Alvarez J. Hum Rep. 2005, July 20(7): 2031-2032.
Baarends W, et al. Reprod 2001; (121):31-39.
Balhorn R. J. Cell Biol. 1982 May; 93(2):298-305.
Brown D B., et al. J Exp Zool. 1987 (242):215-231.
Brown D B, Miskimins K, Ruddle F. J Exp Zool. 1991; (258): 263-272.
Burkman L J, et al. Fertil Steril. 1988 April; 49(4):688-697.
Calamera J, et al. Mol Reprod Dev. 2003 December; 66(4): 422-430
Di Meglioa S, et al. Biochim Bioph Acta 2004; (1692):35-44.
Esterbauer H, Free Radic Biol Med. 1991; 11(1):81-128.
Esterbauer H., Am J Clin Nutr. 1993; May; 57(5 Suppl):779S-785S; discussion 785S-786S.
Evenson D P, et al. Chromosoma. 1980; 78(2):225-238.
Fraczek M, et al. Ginekol Pol. 2001 February; 72(2):73-79
Franken D. Biosci. 1998; (3, e24) December 15.
Furlong L, Jeffrey D. Harris, Vazquez-Levin H. Fertil Steril 2005; (83): 1780-1790.
Gil-Guzman E, et al. Hum Reprod. 2001 September; 16(9): 1922-1930.
Gomez E, et al. Int J. Androl. 1998; April; 21(2):81-94.
Gorczyca W, et al. Exp Cell Res. 1993 July; 207(1):202-205.
Govin J, et al. Eur. J. Biochem. 2004; (271):3459-3469.
Hansen A, et al. DNA Rep. 2005; (7): 1-9.
Heindryck B, et al. Hum Reprod. 2005; 20(8): 2237-2241.
Hodgen G D, et al. J In Vitro Fert Embryo Transf. 1988 December; 5(6):311-313.
Iseki S. DNA strand breaks in rat tissues as detected by in situ nick translation. Exp Cell Res. 1986 December; 167(2): 311-326.
Kemal Duru N, et al. Fertil Steril. 2000; December; 74(6): 1200-1207.
Koksal I T, et al. Potential role of reactive oxygen species on testicular pathology associated with infertility. 2003 June; 5(2):95-99.
Kunkle M, et al. J Exp Zool. 1978 March; 203(3):371-380.

Lahn B, et al. PNAS 2002; (99): 8707-8712.
Langlais J, et al. Gam Res. 1985; (12):183-224.
Le Lannou D, et al. J Reprod Fertil 1988; (84): 551-556.96.
Lemkecher T, et al. Gynecol Obstet. Fertil. 2005; January-February; 33(1-2):2-10.
Ludovic M, et al. Biol Rep 2004; (70): 910-918.
Loft S, et al., Hum Reprod 2003; (18):1265-1272.
Longo F J, et al. Dev Biol. 1991 November; 148(1):75-86.
Lohka M J, et al. Science. 1983 May 13; 220(4598):719-721.
Lopes S, et al. Fertil Steril 1998; (69):528-532.
Martins S G, et al. Int J. Androl. 2003; October; 26(5):296-304.
Matsumoto K, et al. Mol Cell Biol. 1999; October; 19(10): 6940-6952.
Matsumoto Y, et al. Mol Cell Biol. 1989 September; 9(9): 3750-3757.
Matsumoto Y, et al. Mol Cell Biol. 1994 September; 14(9): 6187-6197.
Mazia, D J Cell Comp Physiol [Suppl] 1963; (62):123-140.
Misro M M, et al. Int J. Androl. 2004; April; 27(2):82-87.
Naish S J, et al. Gamete Res. 1987 October; 18(2):109-120.
Naish S J, et al. Biol Reprod. 1987; 36:245-253.
Naz R K, et al. Reprod Biol Endocrinol. 2004; Nov. 9; 2(1): 75.
Ochsendorft F R. Hum Reprod. 1999; (5):399-420.
Oda N, et al. J Biol. Chem. 1996 Jun. 7; 271(23):13816-13820.
Ollero M. Mol Reprod Dev. 2000; March; 55(3):326-334.
Palermo, G., et al. Lancet, 340, 17-18.
Perreault S D, et al. J Exp Zool. 1982 Dec. 10; 224(2):253-257.
Perreault S D, et al. Dev Biol. 1984 January; 101(1):160-167.
Perreault S D, et al. Biol Reprod. 1987. 36: 239-244.
Perreault S D, et al. Dev Biol. 1988 January; 125(1):181-186 a.
Perreault S D, et al. Biol Reprod. 1988 August; 39(1):157-167b.
Perreault S D. Mutat Res. 1992 December; 296(1-2):43-55.
Philpott A, et al. Cell. 1991; May 17; 65(4):569-578.
Philpott A, et al. Cell 1992; May 29; 69(5):759-767.
Ramos L, et al. Hum Rep. 2001; 16(8):1703-1707.
Romeo C, et al. Hum Reprod. 2003; January; 18(1):26-29.
Sailer B L, et al. J. Androl. 1995 January-February; 16(1):80-87.
Saleh R A, et al. J Androl 2002; (23):737-752a.
Saleh R, et al. J of Androl. 2002; 23(6):737-752.
Saleh R A, et al. Fertil Steril 2002; 78 (6):1215-1224.
Svoboda D L, et al. J Biol. Chem. 1993 Jan. 25; 268(3):1931-1936.
Tanaka H, et al. Mol Hum Reprod 2003; 9 (2):69-73.
Tavilani H, et al. Clin Chim Acta. 2005 June; 356(1-2):199-203.
Tirado E, et al. Abstract Presented at the International Federation of Fertility Societies (IFFS) World Congress on Fertility and Sterility held in Montreal, Canada, May 23-28, 2004.
Turkyilmaz Z, et al. Int J. Androl. 2004; June; 27(3):183-187.
Twigg D A, et al. Hum Reprod 1998; (13):338-348.
Van Kooij R J. et al. Int J. Androl. 2004; June; 27(3):140-146.
Wang X, et al. Fertil Steril. 2003; September; 80 (3):531-535.
Webb G C, et al. Fabb S A. Cytobios. 1985; 43(172-173):159-165.
Williams C; et al. Fertil Steril 2005; 83(4):929-936.
Zhi Hong Lu, et al. J of Cell Sci. 1997 (110):2745-2758.
Agarwal A, et al. Reprod Biomed Online. 2005 November; 11(5):641-650.
Alvarez J G, et al. Fertil Steril. 2002 August; 78(2):319-329.
Askienazy-Elbhar M., et al. Gynecol Obstet. Fertil. 2005 September; 33(9):691-697.
Babior B, et al. Biophys. 2002; (397): 342-344.
Backer M, et al. Protoplasma 2003; (221):145-151.
Bartoov, B., et al. Arch Androl. 1980; (5):305-322.
Binks S, et al. Immunol Invest 1999; (28): 353-364.
Choi H S. et al. J Immunoassay Immunochem. 2006; 27(1): 31-44.
Chohan K R, et al. J. Androl. 2006 January-February; 27(1): 53-59.
Comhaire F H, et al. Hum Reprod Update. 1999; September-October; 5(5):393-398.
Esfandiari N, et al. J. Androl. 2003; 24(6):862-870.
Evenson D P. J of Androl. 2000; (21): 739-745.
Fraczek M, et al. et al. Int J. Androl. 2004; April; 27(2):69-75.
Gamido N, et al. Asian J Androl 2004; March; (6):59-65.
Jedrzejczak P, et al. Int J. Androl. 2005; October; 28(5):275-283.
Kurutas E B, et al. Mediators Inflamm. 2005; Aug. 31(4):242-244.
Moskovtsev S I, et al. Arch Androl. 2005 January-February; 51(1):33-40.
Reichart M, et al. Andrologia. 2000 May; 32(3):139-145.
Russell M W, et al. Microbes Infect. 2002 May; 4(6):667-77.
Schaad N C, et al. Hum Reprod 1996; (11): 561-565.
Sikka S C, et al. Int J. Androl. 2001; June; 24(3):136-141.
Tirado E, et al. Effect of in vivo Oxidative Stress Generated During Acute Infection/Inflammation on Human Sperm Activation Poster Presented at the 60th Annual Meeting of the American Society for Reproductive Medicine Held in Philadelphia, Pa., October 17-20, 2004.
Wang A, et al. Arch Androl. 1997; July-August; 39(1):11-17.
WHO Laboratory manual for the examination of human semen and sperm- and sperm-cervical mucus interaction. Fourth Edition. Cambridge University Press. 1999.
Aitken R J, et al. Analysis of sperm function following exposure to the ionophore A23187. Comparison of normospermic and oligozoospermic men. Journal of Andrology 5:321-329.
Bar-Charma N, et al. Urological Clinics of North America 21:433-446.
Chan S Y, et al. TEST-egg yolk buffer storage increases the capacity of human sperm to penetrate hamster eggs in vitro. International Journal of Andrology 10(3):517-524.
Cohen J, et al. Life Sciences 30(11):899-904.
Cohen J. Sorting Out Chromosome Errors. Science 296: 2164-2166, 2002.
DeJonge C J, et al. Gamete Research 23:387-397.
Honea K L, et al. Journal of Assisted Reproduction and Genetics 10(4):255-260.
Hoyes K P, et al. Radiat Res. 1994 August; 139(2):185-93.
Irvine D S. Andrologia 2000 September; 32(4-5):195-208.
Irvine D S, et al. J Androl 2000 January-February; 21(1):33-44.
Johnson A R, et al. Keel and Webster (eds). CRC Press, Boca Raton, pp. 135-147.
Johnson A R, et al. Fertility and Sterility 41(4):603-608.
Johnson, A R, et al. B Keel, B Webster. Boca Raton, CRC Press, 1990:135-147.
Karaca A G, et al. Poult Sci. 2002 December; 81(12):1892-7.
Kunzle R, et al. Fertil Steril. 2003 February; 79(2):287-91.
Massaad C, et al. Eur J Obstet Gynecol Reprod Biol. 2002 Jan. 10; 100(2):127-37.
Merryman D C, et al. Poster presentation, American Society for Reproductive Medicine.
Moline J M, et al. Environ Health Perspect. 2000 September; 108(9):803-13.

Rogers B J, et al. Fertility and Sterility 32:664-670.
Samocha-Bone D, et al. Mol Hum Reprod 1998 February; 4(2):133-7.
Sawyer, D E, et al. 2000; Toxicology Letters 114:19-26.
Stewart Irvine, et al. British Medical Journal 1996 vol. 312: 7029:467-471.
Tirado, E. E., et al. Poster Presentation (P-360) at the 59th annual meeting of the American Society for Reproductive Medicine. San Antonio, Tex., Oct. 11-15, Fert. Steril. 80 (Sup. 3):5240, 2003.
Wong W Y, et al. Fertil Steril. 2000 November; 74(5):930-5.
Yanagimachi R (1981). Plenum Press, New York, p. 81-187.
Yanagimachi R, et al. Biology of Reproduction 15:471-476.
U.S. Pat. No. 5,358,847—Brown et al.
U.S. Pat. No. 5,770,363—Brown et al.
U.S. Pat. No. 5,919,621—Brown et al.

What is claimed is:

1. A method for determining if a donor test sperm sample is appropriate for use in an assisted reproductive technology (ART) comprising:
    (a) assessing sperm DNA accelerated decondensation (SDAD) rate of the test sperm sample and comparing said rate to a control sperm SDAD rate to provide a test sperm SDAD score comprising:
    incubating the test sperm sample in a non-mammalian egg extract capable of supporting human sperm DNA decondensation and sperm DNA synthesis for a defined incubation period of about 5 minutes; determining a test sperm SDAD percentage from the percent of DNA decondensed in the test sperm sample; and comparing the test sperm SDAD percentage to a control sperm SDAD percentage to provide a test sperm SDAD score, wherein a test sperm SDAD score that is 120% or greater identifies a test sample demonstrating an abnormal test sample SDAD score; and
    (b) assessing the test sperm, sample to determine a test sperm DNA fragmentation index (DFI) comprising:
    determining a ratio of broken DNA to unbroken DNA in the test spent1 sample to provide a test sperm DNA fragmentation index (DFI), wherein a test sperm sample having a DFI of 30 or greater-identifies an abnormal test sample DFI and a DFI of less than 30 identifies a normal DFI and
    (c) assessing the donor test sperm for an appropriate assisted reproductive technology (ART) of intracytoplasmic sperm injection (ICSI), intrauterine insemination (ILA) or IVF-embryo transfer,
    wherein a donor test sperm demonstrating an SDAD score of 120% or greater (abnormal) and a DFI of greater than 30 (abnormal) is unsuitable as a donor for use in an intracytoplasmic sperm injection (ICSI) procedure, and wherein a donor test sperm having a DFI of less than 30 (normal) and an SDAD that is not greater than 120% (normal) is suitable for use in an assisted reproductive technology of intracytoplasmic sperm injection (ICSI), intrauterine insemination (IUI) or IVF-embryo transfer.

2. The method of claim 1 wherein the donor test sperm sample is a human sperm sample.

3. The method of claim 1 wherein the non-mammalian egg extract is a frog egg extract.

4. The method of claim 3 wherein the non-mammalian egg extract is *Xenapus laevis* frog egg extract.

5. A method for determining the suitability of a donor sperm for use in an intracytoplasmic sperm injection (ICSI) procedure comprising:
    (a) assessing a sperm sample of the donor sperm for sperm DNA accelerated decondensation (SDAD) after an about 5 to 10 minute incubation period in a frog egg extract, and comparing the test sample SDAD to a control sperm sample SDAD to provide a test sample SDAD score;
    (b) assessing sperm DNA fragmentation present in a test sperm sample of the donor sperm to provide a test sperm DNA fragmentation index (DFI), and
    (c) determining the suitability of the donor sperm for use in an ICSI procedure, wherein a test sperm sample having a SDAD score of less than 120% (normal) and a DFI of 30 or greater identifies the donor sperm as suitable for use in an intracytoplasmic sperm injection (ICSI) procedure.

6. A method for assessing the reproductive health of sperm from a human male comprising:
    (a) assessing a test sperm sample for sperm DNA accelerated decondensation (SDAD) to identify the test sperm sample as having a normal SDAD score or an abnormal SDAD score, comprising:
    incubating the test sperm sample in a non-mammalian egg extract capable of supporting human sperm DNA decondensation and sperm DNA synthesis for an incubation period of 5 to 10 minutes;
    determining a test sperm DNA accelerated decondensation (SDAD) value from the percent of decondensed DNA in the test sperm sample present at the end of the incubation period; and
    comparing the test sperm DNA accelerated decondensation (SDAD) value to a control sperm DNA accelerated decondensation (SDAD) value obtained at an incubation period of 5 to 10 minutes to provide a test sperm DNA accelerated decondensation (SDAD) score,
    wherein a test sperm SDAD score that is less than 120% of a control sperm SDAD score identifies a test sample demonstrating a normal sperm DNA decondensation assessment SDAD score, and wherein a test sperm decondensation percentage having SDAD score that is 120% or greater than a control sperm SDAD score percentage identifies a test sample demonstrating an abnormal SDAD score; and
    (b) assessing the test sperm sample for reproductive health of the human male, wherein an accelerated decondensation rate greater than 120% of a control sample is indicative of poor reproductive health and is unsuitable as a donor for ICSI, IVF and IUI.

7. The method of claim 6 wherein the donor test sperm sample is a human sperm sample.

8. A method for determining if a test sperm sample is appropriate for use in an assisted reproductive technology (ART) comprising:
    (a) assessing a test sperm DNA accelerated decondensation (SDAD) rate of the sperm sample and comparing said rate to a control sperm DNA accelerated decondensation rate comprising:
    incubating the test sperm sample in a non-mammalian egg extract capable of supporting human sperm DNA decondensation and sperm DNA synthesis for an incubation period of 5 to 10 minutes, and determining the amount of decondensed DNA to provide a test sperm SDAD score;
    comparing the test sperm SDAD score to a control sperm SDAD score, and determining if the test sperm SDAD is 120% or greater than the control sperm SDAD;
    (b) assessing a sperm DNA fragmentation index (DFI) value of the test sperm sample by determining the ratio of broken DNA to unbroken DNA in the test sperm sample to provide a test sperm DNA fragmentation (DFI) value, and determining if the test sperm DFI value is 30 or less;

(c) assessing the test sperm sample for sperm DNA decondensation (SDD) to provide a test sperm SDD score, wherein said SDD provides for a measure of sperm PNA decondensation in a non-mammalian egg extract capable of supporting human sperm DNA decondensation and sperm DNA synthesis after an incubation period of about 15 minutes, and comparing the test sperm SDD value to a control sperm SDD value to provide a test sperm SDD score, wherein a test sperm SDD score of less than 80% identifies an abnormal test sample SDD score and an SDD score of at least 80% identifies a normal SDD score; and (d) selecting an appropriate assisted reproductive technology (ART) procedure, wherein a test sperm sample having an SDAD score that is 120% or greater than the control sperm SDAD and a DFI of less than, equal to, or greater than 30, indicates the sperm is unsuitable for IUI, IVF or ICSI; and wherein a test sperm sample having an SDAD score that is less than 120% compared to the control sperm SDAD (normal) and a DFI of 30 or less (normal), and a SDD score that is at least 80% (normal) indicates the sperm is suitable for IUI, IVF or ICSI.

9. The method of claim 8 wherein the non-mammalian egg extract is a frog egg extract.

10. The method of claim 8 wherein the SDAD incubation period is about 5 minutes.

11. The method of claim 8 wherein the frog egg extract is a *Xenopus laevis* or *Rana pipiens* frog egg extract.

12. The method of claim 8 wherein the frog egg extract is *Xenopus laevis* frog egg extract.

13. A method of assessing reproductive health of a human sperm sample from a patient for use in an ICSI procedure comprising assessing a DFI score, an SDAD score and a SDD score for a test sample from the patient as provided in claim 8, wherein a DFI score of 30 or less (normal), or greater that 30 (abnormal), an SDAD score of less than 120% (normal), and an SDD score of less than 80% (abnormal) indicates the sperm is useful for an ICSI procedure, and wherein a sample having a DFI score of greater than 30 (abnormal), or 30 or less (normal), an SDAD score of less than 120% or great (abnormal), and an SDD score of less than 80% (abnormal), indicates the sperm sample is not useful for an ICSI procedure.

* * * * *